United States Patent
Mandel

(10) Patent No.: US 11,464,798 B2
(45) Date of Patent: *Oct. 11, 2022

(54) VACCINE CONTAINING CANCER CELLS INACTIVATED BY PHOTODYNAMIC TREATMENT WITH METAL-BASED COORDINATION COMPLEXES, AND IMMUNOTHERAPY METHOD USING SAME

(71) Applicant: THERALASE BIOTECH INC., Wilmington, DE (US)

(72) Inventor: Arkady Mandel, Toronto (CA)

(73) Assignee: THERALASE TECHNOLOGIES INC., Toronto (CA)

( * ) Notice: Subject to any disclaimer, the term of this patent is extended or adjusted under 35 U.S.C. 154(b) by 532 days.

This patent is subject to a terminal disclaimer.

(21) Appl. No.: 16/610,991

(22) PCT Filed: May 11, 2018

(86) PCT No.: PCT/US2018/032274
§ 371 (c)(1),
(2) Date: Nov. 5, 2019

(87) PCT Pub. No.: WO2018/209203
PCT Pub. Date: Nov. 15, 2018

(65) Prior Publication Data
US 2020/0222450 A1    Jul. 16, 2020

Related U.S. Application Data

(60) Provisional application No. 62/504,580, filed on May 11, 2017.

(51) Int. Cl.
| *A61K 33/24* | (2019.01) |
| *A61K 31/4745* | (2006.01) |
| *A61P 35/00* | (2006.01) |
| *A61K 39/39* | (2006.01) |
| *A61K 39/00* | (2006.01) |

(52) U.S. Cl.
CPC .......... *A61K 33/24* (2013.01); *A61K 31/4745* (2013.01); *A61K 39/0011* (2013.01); *A61K 39/39* (2013.01); *A61P 35/00* (2018.01); *A61K 2039/5152* (2013.01)

(58) Field of Classification Search
CPC ............. A61K 33/24; A61K 31/4745; A61K 39/0011; A61K 39/39; A61K 2039/5152; A61P 35/00
See application file for complete search history.

(56) References Cited

U.S. PATENT DOCUMENTS

| 6,156,305 A | 12/2000 | Brauker et al. |
| 6,962,910 B2 | 11/2005 | Brewer et al. |
| 7,612,057 B2 | 11/2009 | Brewer et al. |
| 8,148,360 B2 | 4/2012 | Brewer et al. |
| 8,445,475 B2 | 5/2013 | Brewer et al. |
| 8,834,899 B2 | 9/2014 | Friedberg |
| 9,737,565 B2 * | 8/2017 | Mandel ................ A61K 9/0009 |
| 10,111,936 B2 * | 10/2018 | Mandel ................ A61N 5/062 |
| 10,335,608 B2 | 7/2019 | Mandel et al. |
| 2007/0025958 A1 | 2/2007 | Hadden |
| 2012/0088729 A1 | 4/2012 | Zhang et al. |
| 2014/0178438 A1 | 6/2014 | Sahin et al. |
| 2015/0093416 A1 | 4/2015 | Hanna, Jr. |
| 2016/0206653 A1 | 7/2016 | Mandel |
| 2016/0206725 A1 | 7/2016 | Hogset et al. |
| 2017/0042976 A1 | 2/2017 | Mandel |

FOREIGN PATENT DOCUMENTS

| WO | 2013158550 A1 | 10/2013 |
| WO | 2014145428 A2 | 9/2014 |

OTHER PUBLICATIONS

Carrasco-Marin et al., "Oxidation of defined antigens allows protein unfolding and increases both proteolytic processing and exposes peptide epitopes which are recognized by specific T cells", Immunology, vol. 95, pp. 314-321 (1998).

Hunn et al., "Vaccination with Irradiated Tumor Cells Pulsed with an Adjuvant That Stimulates NKT Cells Is an Effective Treatment for Glioma", Clin Cancer Res., vol. 18, No. 23, pp. 6446-6459 (2012).

Rizvi et al., "PDT Dose Parameters Impact Tumoricidal Durability and Cell Death Pathways in a 3D Ovarian Cancer Model", Photochem Photobiol., vol. 89, No. 4, pp. 942-952 (2013).

Steere et al., "Biochemcial and Structural Characterization of Recombinant Human Serum Transferrin from Rice (*Oryza sativa* L.)", J. Inorg Biochem., vol. 116C, pp. 37-44 (2012).

Toes et al., "CD4 T Cells and Their Role in Antitumor Immune Responses", The Journal of Experimental Medicine, vol. 189, No. 5, pp. 753-756 (1999).

Zhang et al., "Expression, purification, and characterization of recombinant human transferrin from rice (*Oryza sativa* L.)", Protein Expr Purif., vol. 74, No. 1, pp. 69-79 (2010).

European Search Report for European Patent Application No. 18799412.4 dated Feb. 11, 2021.

Kaspler et al. "A ruthenium (ii) based photosensitizer and transferrin complexes enhance photo-physical properties, cell uptake, and photodynamic therapy safety and efficacy." Photochemical & Photobiological Sciences 15.4 (2016): 481-495.

* cited by examiner

*Primary Examiner* — Timothy R Rozof
(74) *Attorney, Agent, or Firm* — Caesar Rivise, PC

(57) ABSTRACT

A method for treating a tumor in a patient by administering to the patient an immunogenic composition including antigenic material inactivated by treatment with a metal-based coordination complex and electromagnetic radiation, wherein the immunogenic composition is effective to elicit an immune response to the antigenic material in the patient after administration and the metal-based coordination complex having a specified formula. An immunogenic composition and a method for preparing it are also disclosed.

20 Claims, No Drawings

VACCINE CONTAINING CANCER CELLS INACTIVATED BY PHOTODYNAMIC TREATMENT WITH METAL-BASED COORDINATION COMPLEXES, AND IMMUNOTHERAPY METHOD USING SAME

BACKGROUND OF THE INVENTION

1. Field of Invention

This invention relates to immunotherapy and more particularly to the combination of immunotherapy and photodynamic therapy.

2. Description of Related Art

Immunotherapy is recognized as a promising method for treating cancer with much as yet untapped potential. According to a 2016 recent press release from the USPTO regarding the "Cancer Moonshot" initiative, approximately 900 cancer immunotherapy applications are received annually by the USPTO.

One such application is US 20070025958 A1, which discloses compositions and methods of immunotherapy to treat cancer or other antigen-producing diseases or lesions. The compositions comprise an effective amount of a cytokine mixture, which acts as an adjuvant with the antigen associated with the antigen-producing disease or lesion to enhance the immune response of the patient to the antigen.

US 20150093416 A1 discloses autologous anti-cancer vaccines, wherein tumor cells are excised from a patient, implanted and grown in an immune-compromised animal. The resulting tumor tissue is harvested from the animal, inactivated by gamma radiation and incorporated into a vaccine composition for reinjection into the patient.

Photodynamic therapy (PDT) is another treatment modality showing much promise in the treatment of cancer. The development of new photodynamic compounds (PDCs or photosensitizers, PSs) for photodynamic therapy (PDT) has been increasingly focused on metallosupramolecular complexes derived from metals. For example, WO 2013158550 A1 and WO 2014145428 A2 disclose metal-based PDCs useful as in vivo diagnostic agents, as therapeutic agents for treating or preventing diseases that involve unwanted and/or hyperproliferating cell etiology, including cancer, as agents for treating infectious diseases, and as agents for pathogen disinfection and/or sterilization. U.S. Pat. Nos. 6,962,910, 7,612,057, 8,445,475 and 8,148,360 disclose supramolecular metal complexes capable of cleaving DNA when irradiated low energy visible light with or without molecular oxygen.

Delivery of metal-based coordination complexes and PDCs to biological targets can pose a challenge, which many have attempted to address. See, e.g., U.S. patent application Ser. No. 15/291,025, and the references cited therein.

Combinations of immunotherapy and photodynamic therapy are known. For example, U.S. Pat. No. 8,834,899 B2 discloses a vaccine for mesothelioma generated using photodynamic therapy and its use in methods and compositions for treating mesothelioma.

Despite the foregoing developments, it is desired to provide improved compositions and methods for immunotherapy.

BRIEF SUMMARY OF THE INVENTION

A first aspect of the invention is a method for treating a tumor in a patient, said method comprising administering to the patient an immunogenic composition comprising antigenic material inactivated by treatment with a metal-based coordination complex and electromagnetic radiation, wherein the immunogenic composition is effective to elicit an immune response to the antigenic material in the patient after administration and the metal-based coordination complex is represented by one of the following formulas:

(a) formula (I):

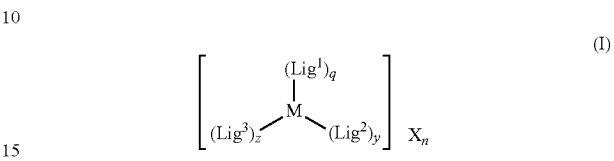

including hydrates, solvates, pharmaceutically acceptable salts, prodrugs and complexes thereof, wherein:

M at each occurrence is independently selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

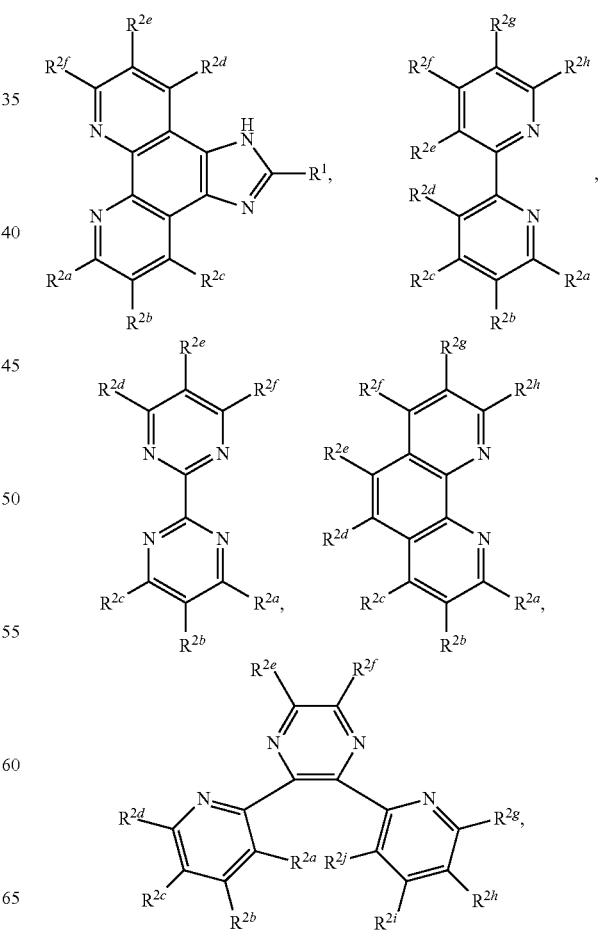

-continued
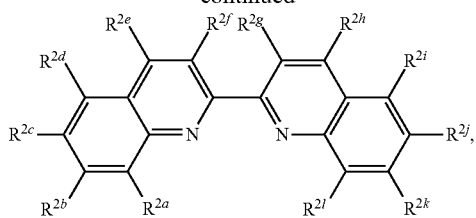
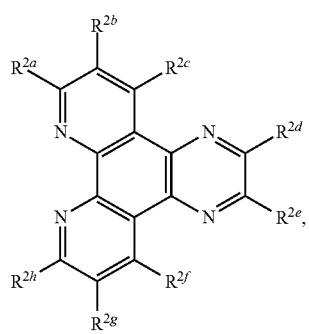
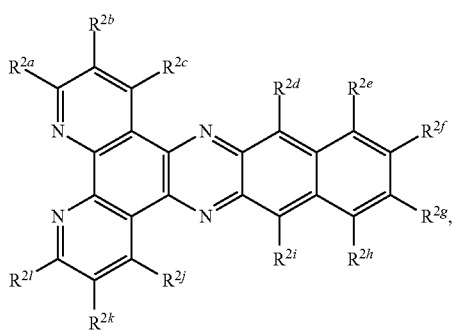
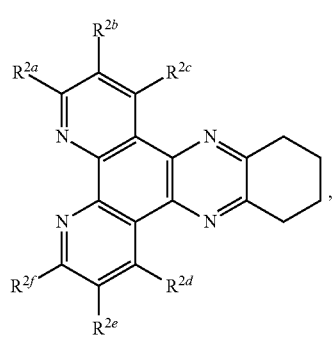
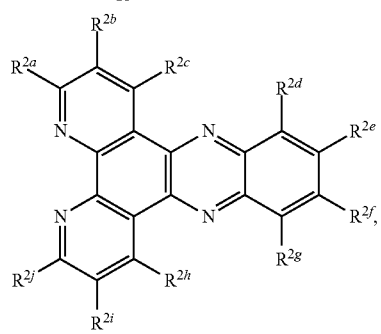
-continued
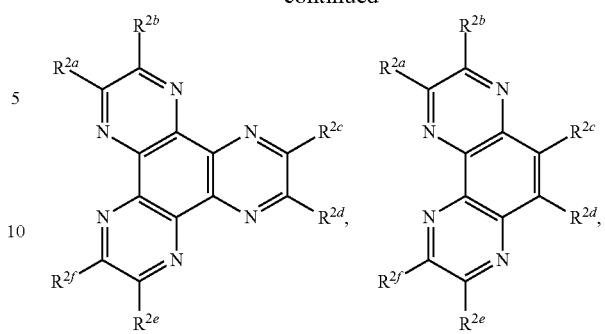
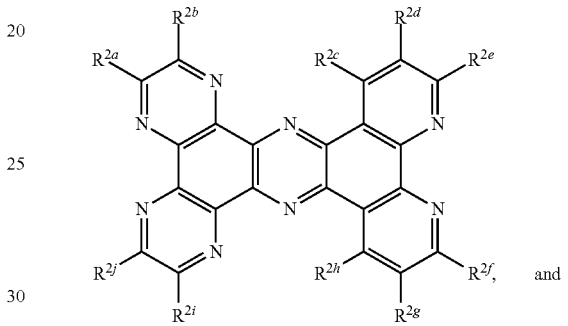
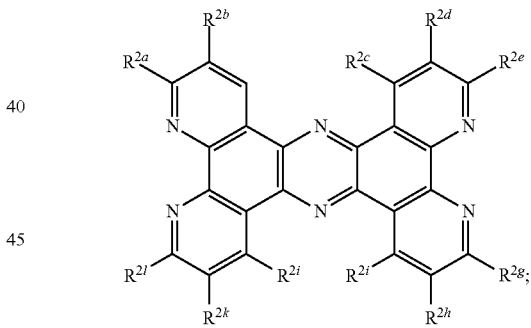
Lig² is a bidentate ligand that at each occurrence is each independently selected from the group consisting of
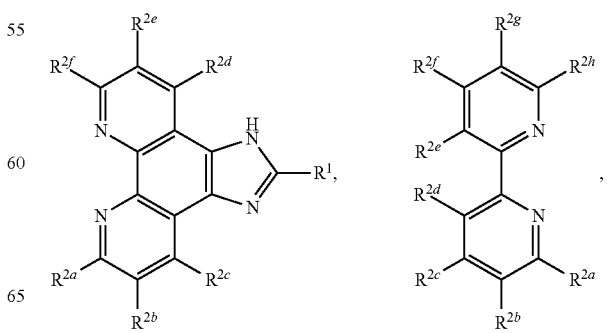

-continued
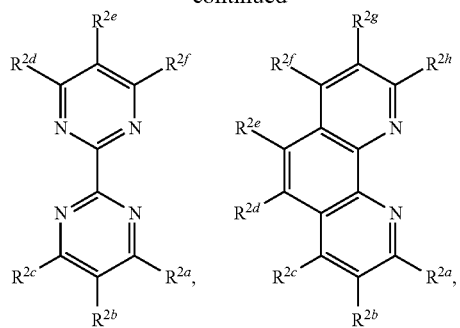
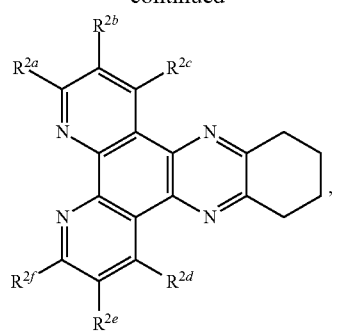
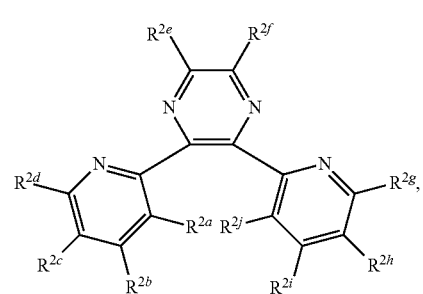
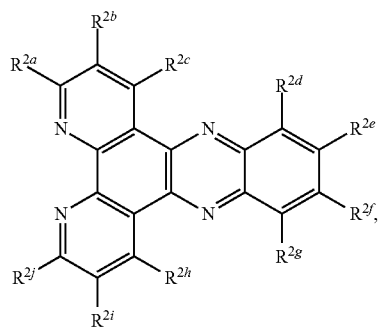
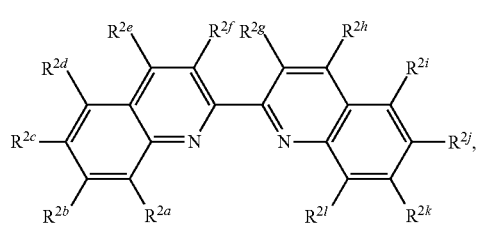
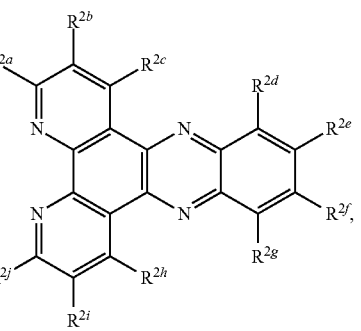
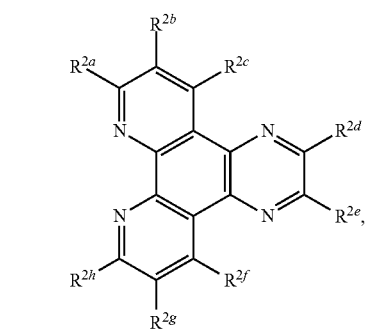
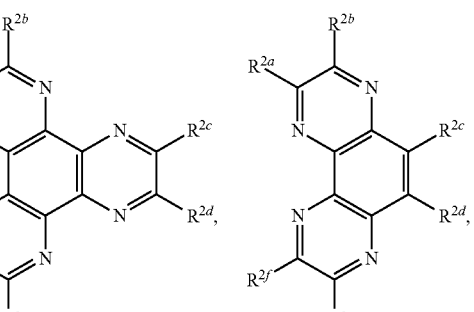
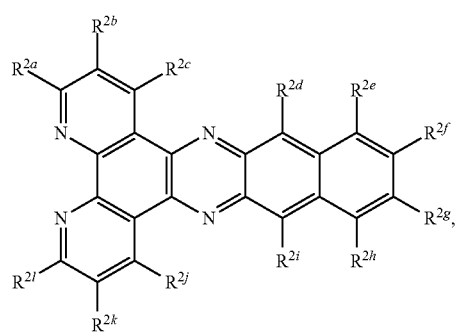
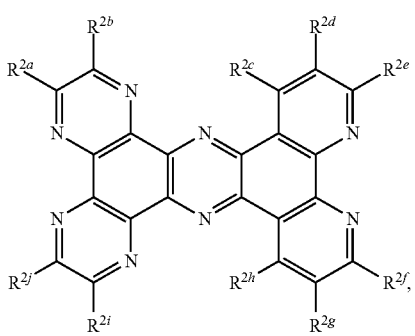, and

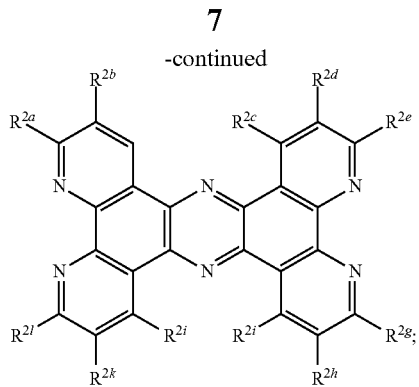
Lig³ is a bidentate ligand that at each occurrence is each independently selected from the group consisting of
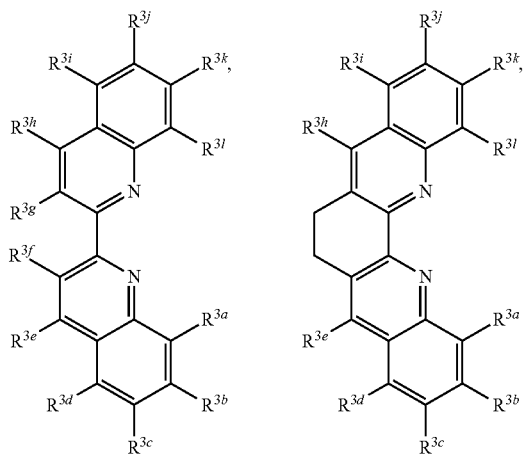
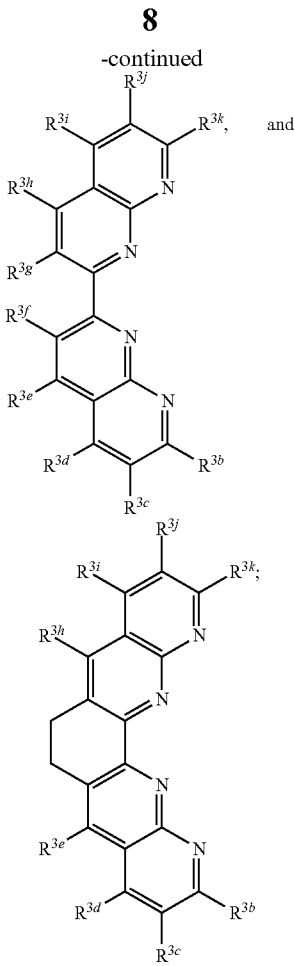
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
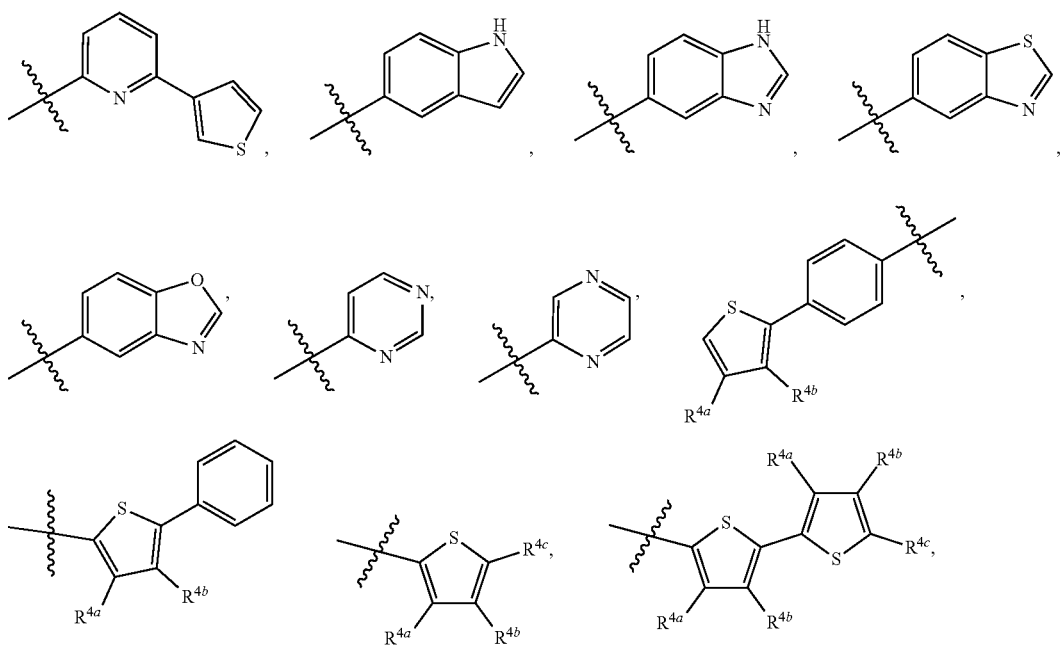

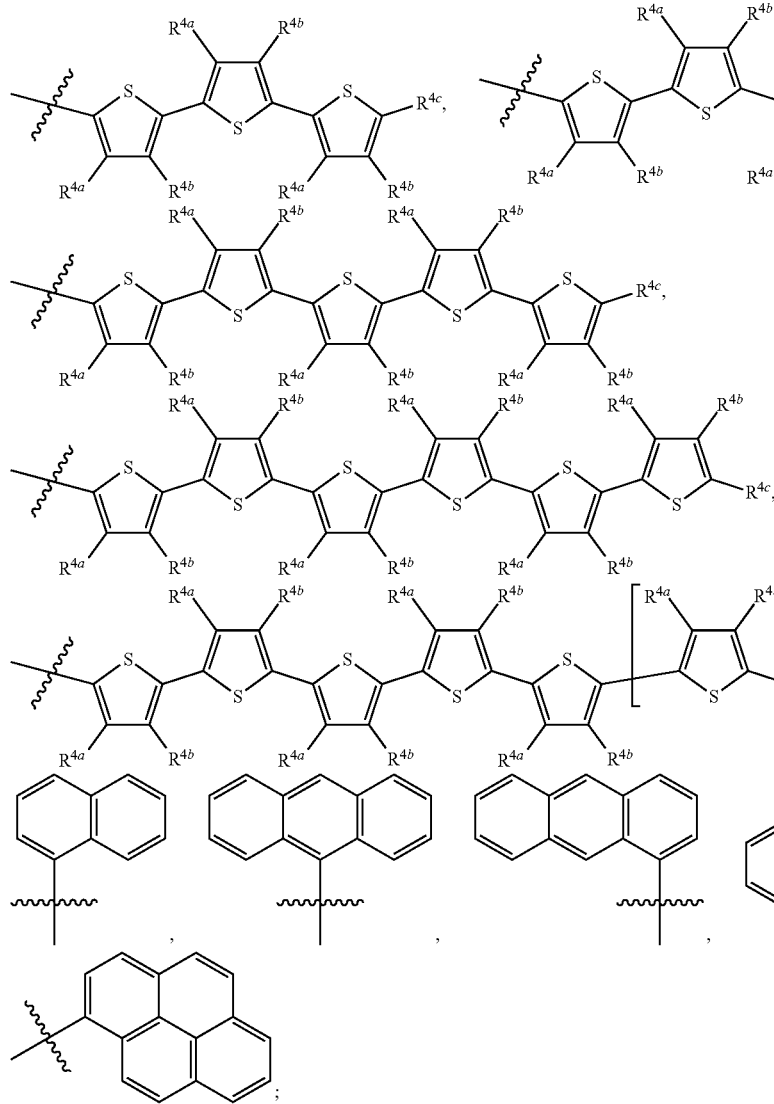
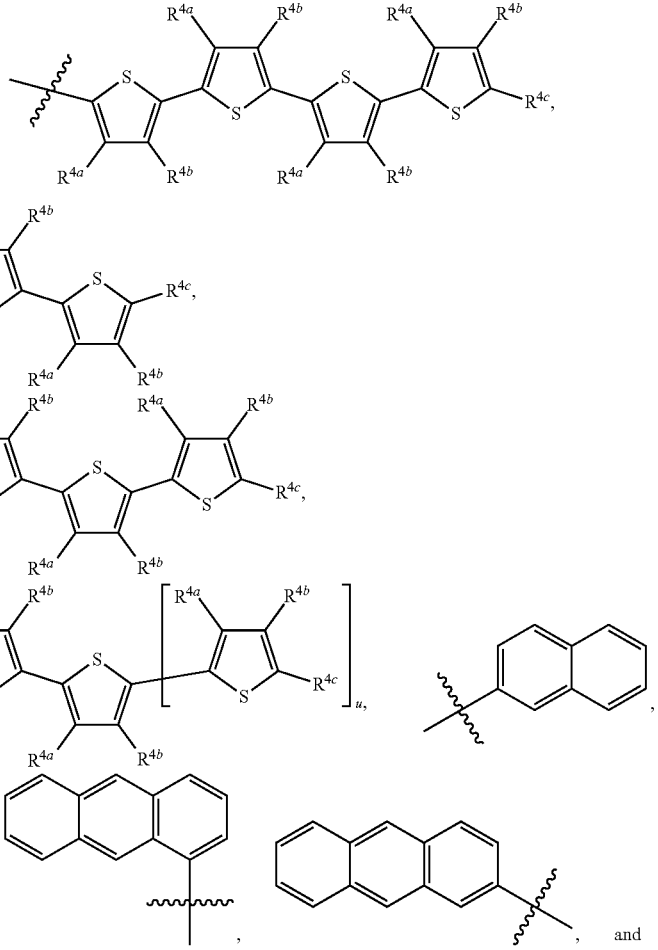

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

(b) formula (VI):

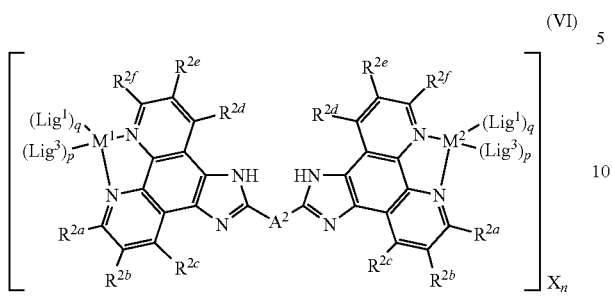

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

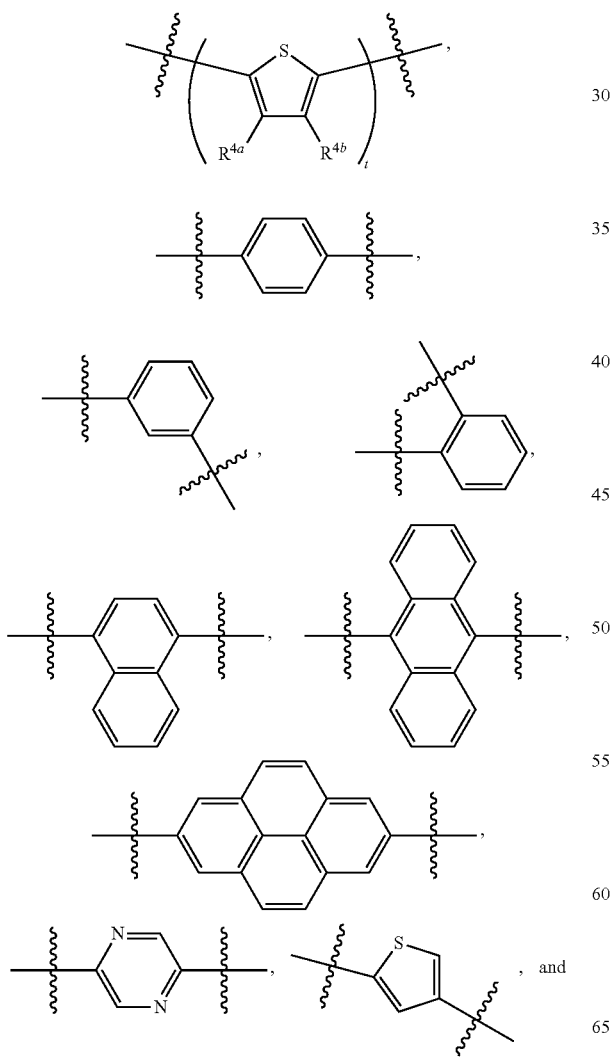

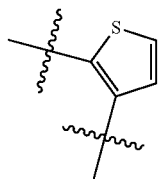

t is an integer;

(c) formula (VIIa):

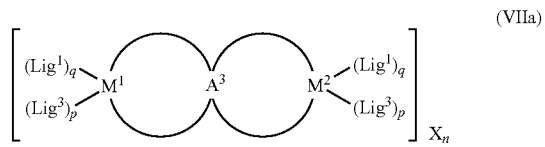

including hydrates, solvates, pharmaceutically acceptable salts, prodrugs and complexes thereof wherein:

$A^3$ is selected from the group consisting of

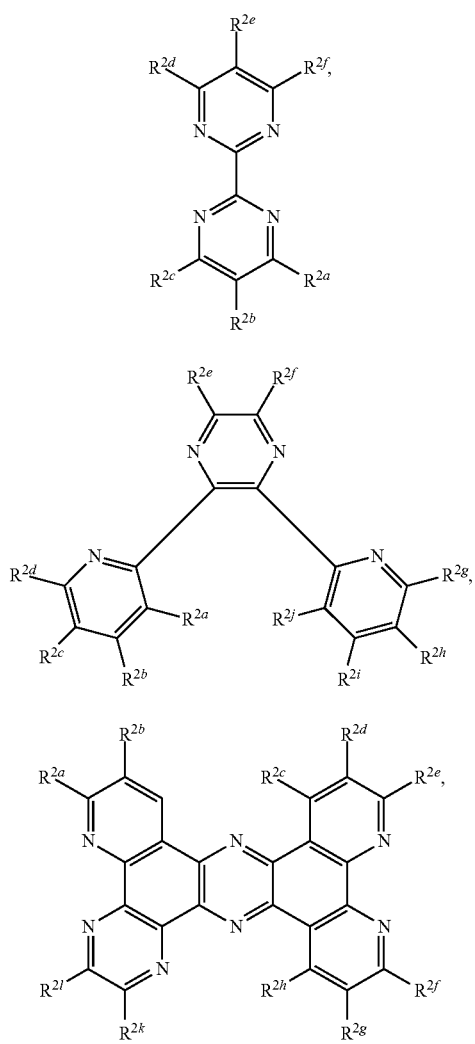

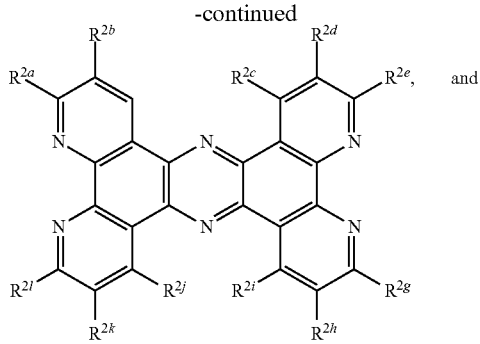
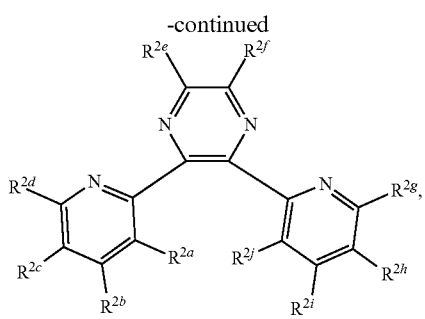
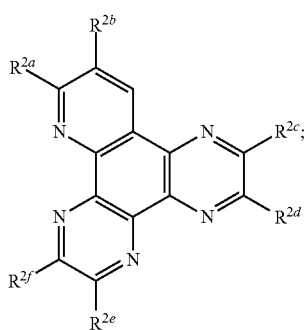
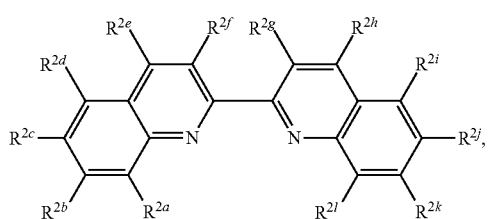
Lig¹ is a bidentate ligand that at each occurrence is each independently selected from the group consisting of
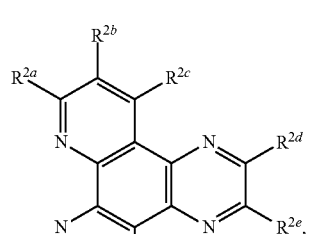
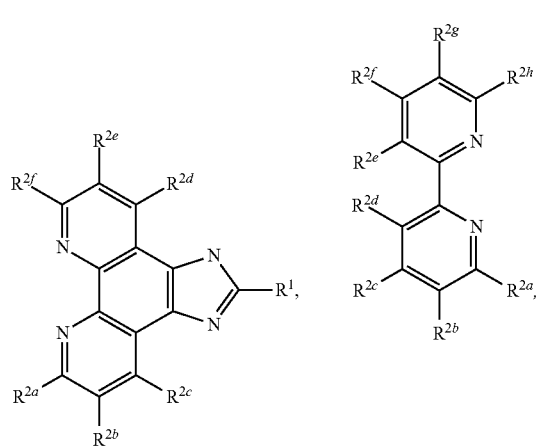
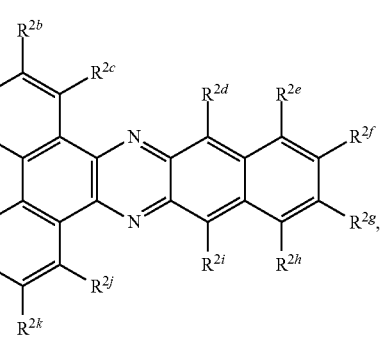
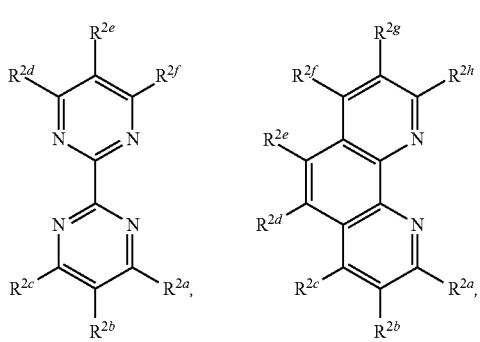
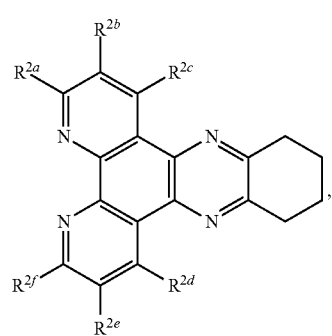

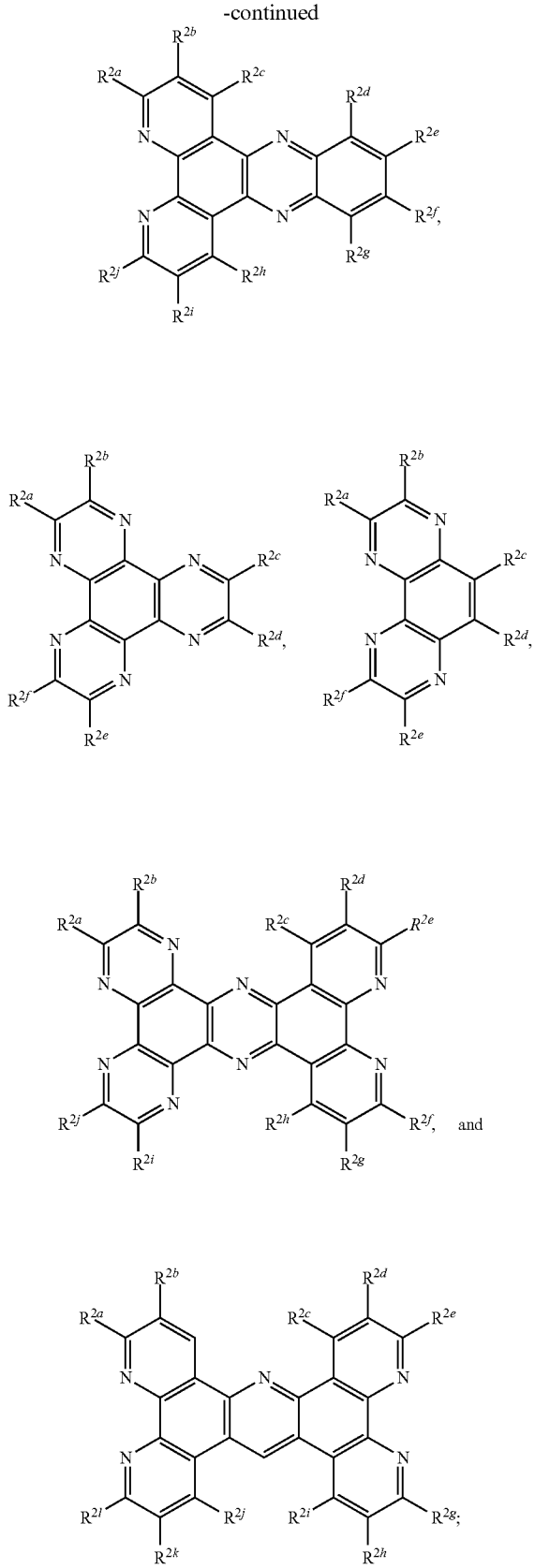
Lig³ is a bidentate ligand that at each occurrence is each independently selected from the group consisting of
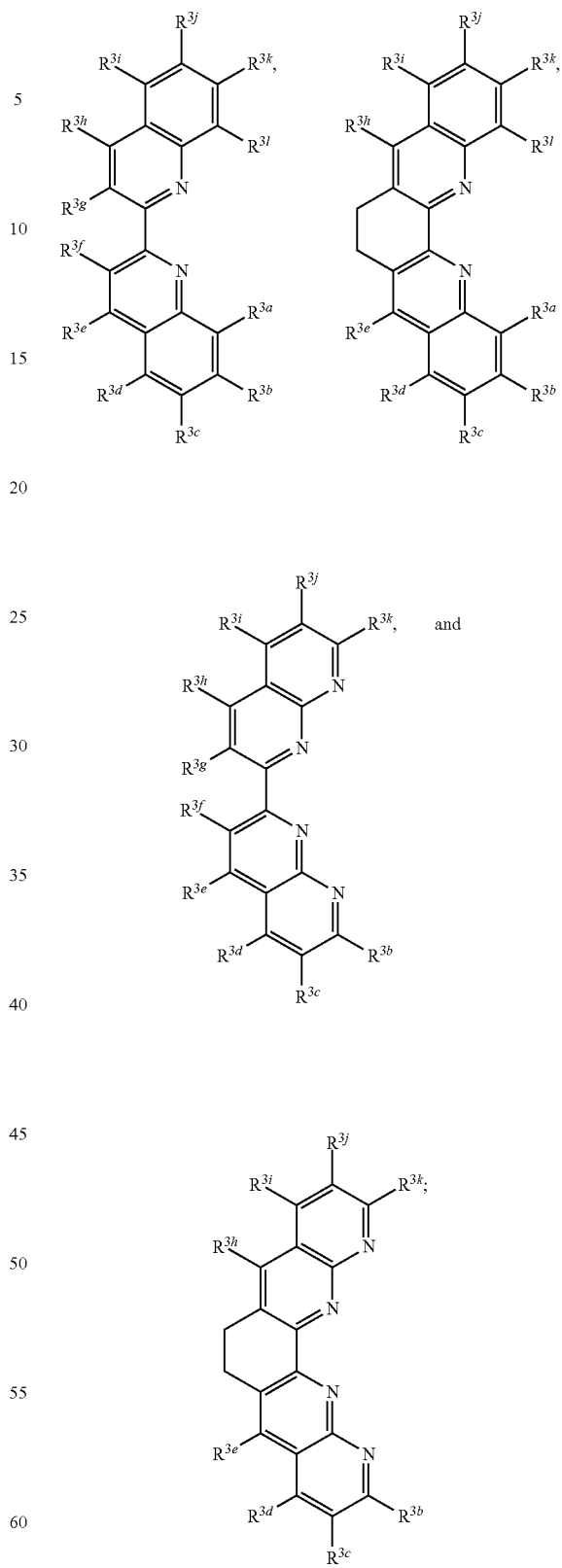
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,

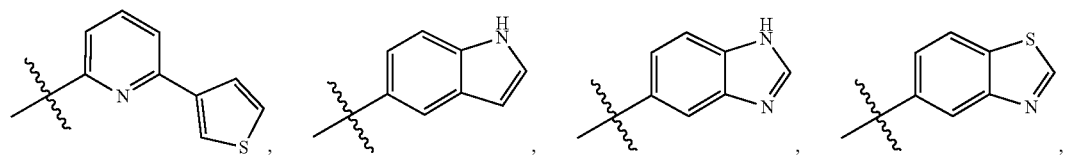
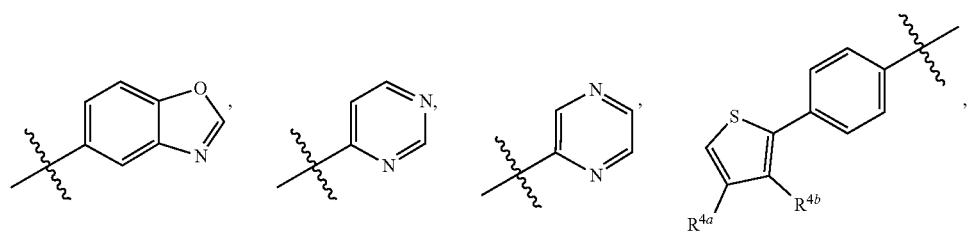
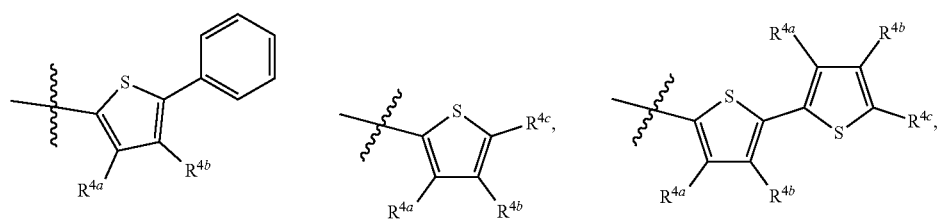
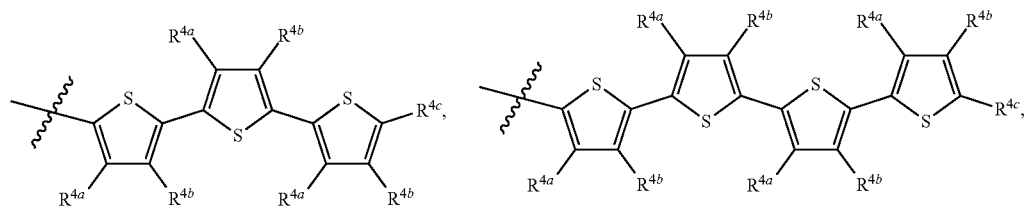
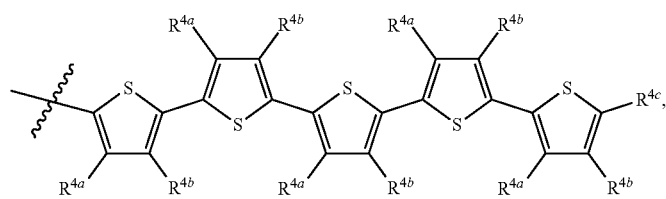
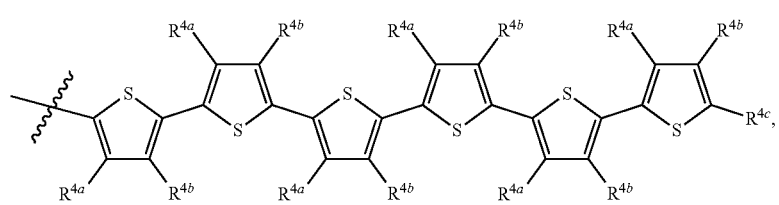

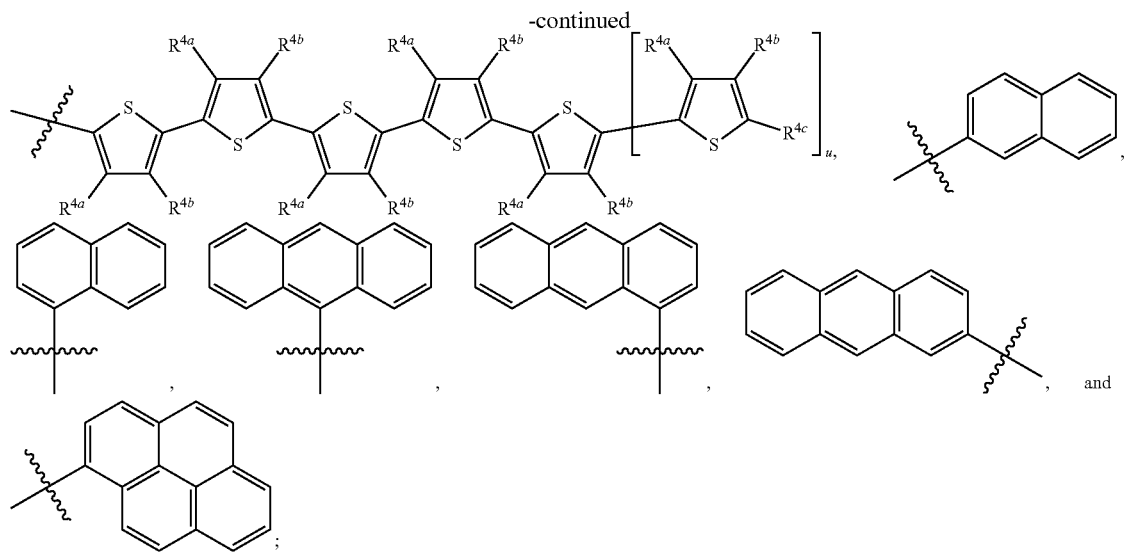

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl p is independently at each occurrence 0, 1, or 2;
q is independently at each occurrence 0, 1, or 2; and
n is 0, 1, 2, 3, 4, or 5.

(d) formula (II):

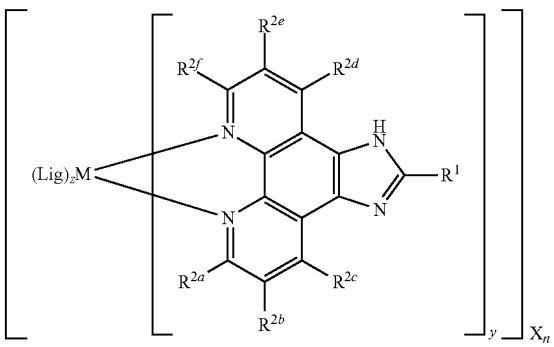

(II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

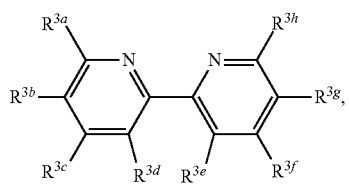

-continued
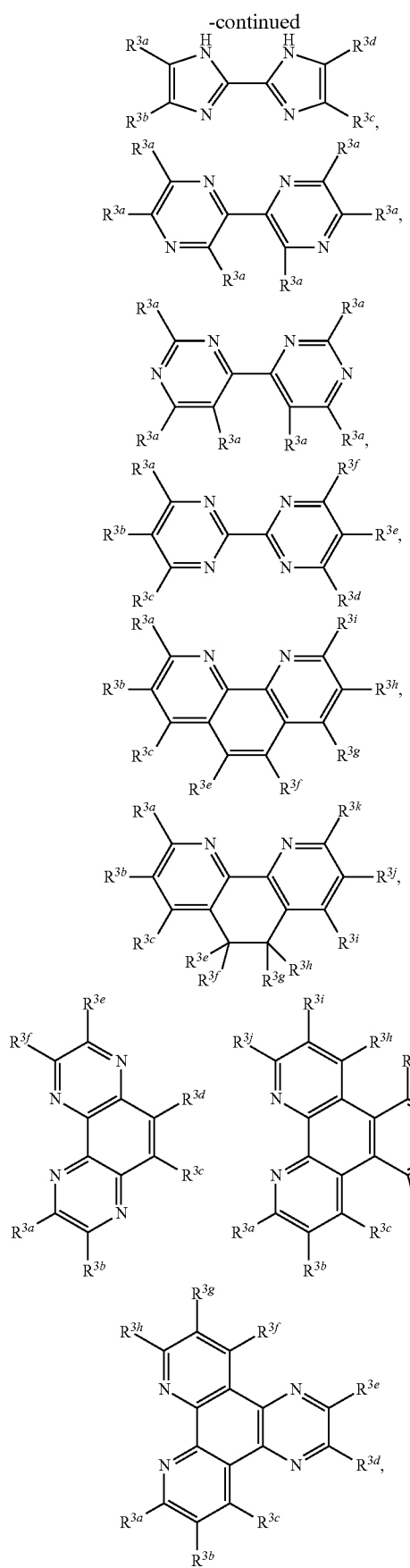
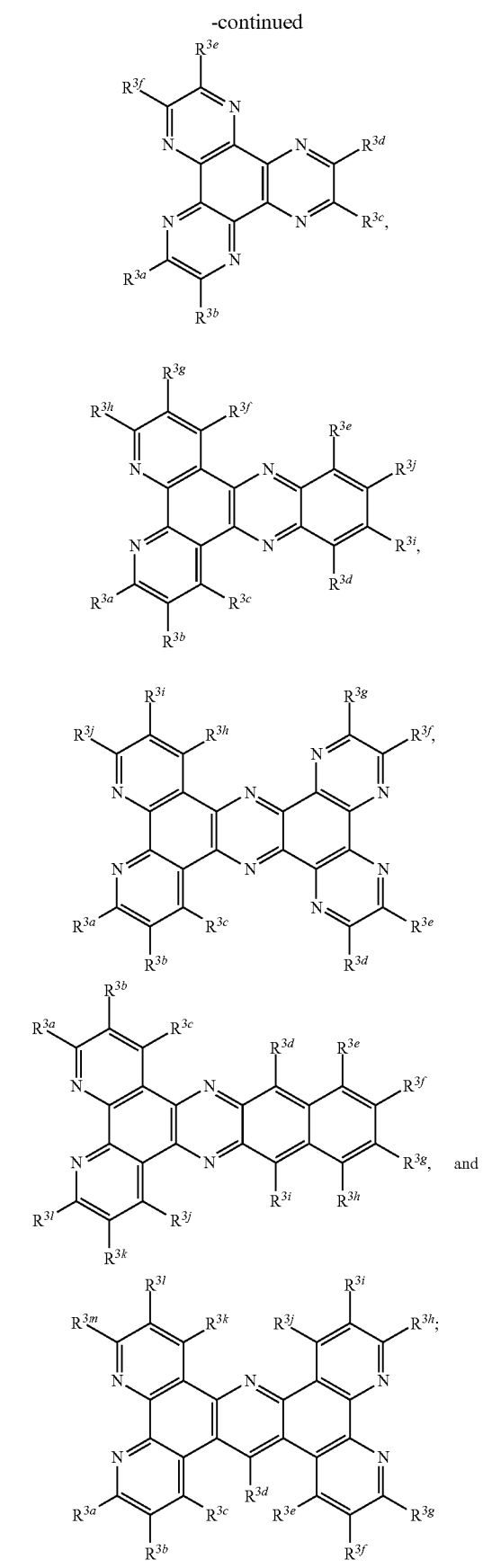

R[1] is selected from the group consisting of

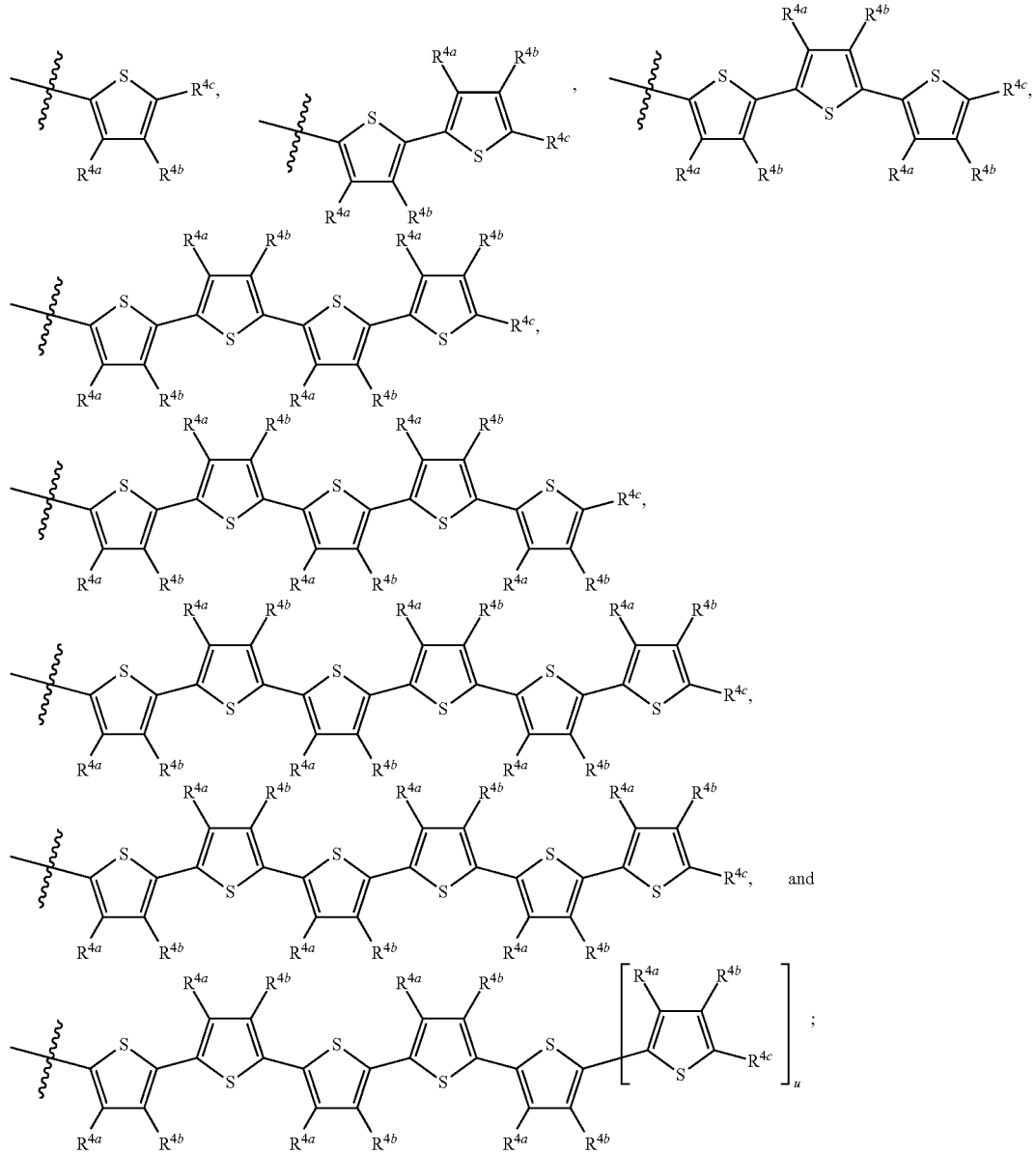

u is an integer;

R[2a], R[2b], R[2c], R[2d], R[2e], and R[2f] at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

R[3a], R[3b], R[3c], R[3d], R[3e], R[3f], R[3g], R[3h], R[3i], R[3j], R[3k], R[3l], and R[3m] at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

R[4a], R[4b], and R[4c] at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

R[4a] and R[4b] at each occurrence on a thiophene ring are taken together with the atom to which they are bound to form an optionally substituted ring having from 6 ring atoms containing 2 oxygen atoms;

R[5] at each occurrence is independently selected from the group consisting of hydrogen and optionally substituted alkyl;

R⁶ at each occurrence is independently selected from the group consisting of hydrogen and optionally substituted alkyl;

R⁷ at each occurrence is independently selected from the group consisting of hydrogen and optionally substituted alkyl; and R⁸ at each occurrence is independently selected from the group consisting of hydrogen and optionally substituted alkyl.

In certain embodiments of the treatment method, the immunogenic composition is prepared by collecting tumor cells from a donor, preparing a composition comprising the tumor cells and the metal-based coordination complex, and exposing the composition to the electromagnetic radiation to provide the immunogenic composition.

In certain embodiments of the treatment method, the electromagnetic radiation is laser light having a wavelength from 500-950 nm.

In certain embodiments of the treatment method, the electromagnetic radiation is X-rays or Gamma rays.

In certain embodiments of the treatment method, the donor is the patient and is a human, and the tumor cells are cancer cells.

In certain embodiments of the treatment method, the metal-based coordination complex further comprises transferrin.

In certain embodiments of the treatment method, M is at least one of Ru, Rh, Os and Ir.

In certain embodiments of the treatment method, the metal-based coordination complex has the structure of formula (II) below:

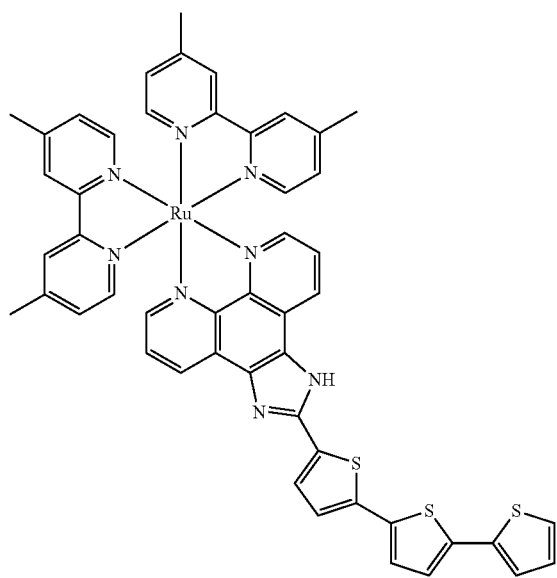

and is sometimes identified herein as TLD1433.

A second aspect of the invention is a method for preparing an immunogenic composition, said method comprising: collecting tumor cells from a donor; preparing a composition comprising the tumor cells and a metal-based coordination complex; and exposing the composition to electromagnetic radiation to provide the immunogenic composition, wherein the immunogenic composition is effective to elicit an immune response to the antigenic material in a patient to whom the immunogenic composition is administered, and the metal-based coordination complex is represented by one of formulas (I), (VI), (VIIa) or (II) above.

In certain embodiments of the preparation method, the electromagnetic radiation is laser light having a wavelength from 500-950 nm.

In certain embodiments of the preparation method, the electromagnetic radiation is X-rays or Gamma rays.

In certain embodiments of the preparation method, the donor is a human and the tumor cells are cancer cells.

In certain embodiments of the preparation method, the metal-based coordination complex further comprises transferrin.

In certain embodiments of the preparation method, M is at least one of Ru, Rh, Os and Ir.

In certain embodiments, the immunogenic composition is incubated with dendritic cells from the patient so as to prepare armed dendritic cells having tumor antigens, the armed dendritic cells are administered to the patient, and/or the armed dendritic cells are co-cultured with CD4+ or CD8+ to provide expanded CD4+ or CD8+ cells which are administered to the patient. In these embodiments, the armed dendritic cells and/or expanded CD4+ or CD8+ cells are optionally administered in combination with transferrin.

A third aspect of the invention is an immunogenic composition comprising inactivated tumor cells, which is prepared by the preparation method of the invention.

In certain embodiments of the immunogenic composition, the metal-based coordination complex further comprises transferrin.

In certain embodiments of the immunogenic composition, M is at least one of Ru, Rh, Os and Ir.

In certain embodiments of the immunogenic composition, the metal-based coordination complex has the structure of formula (II) above.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously For the purposes of the present invention the terms "compound," "analog," and "composition of matter" stand equally well for the inventive compounds described herein, be they photodynamic or not, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "photodynamic therapy" refers to a treatment for destroying cells or modulating immune function, including immune response, of cells and tissue through use of a drug that can be activated by light of a certain wavelength and dose.

As used herein the term "chemotherapeutic compound" refers to a chemical compound with prophylactic, ameliorative and/or curative properties with respect to one or more conditions or diseases.

As used herein, the term "photodynamic compound" refers to a compound that provides photodynamic therapy. Photodynamic compounds are a subset of chemotherapeutic compounds as defined herein.

As used herein, the term "immunotherapy" refers to a treatment which elicits an immune response from a patient so as to prevent, ameliorate or cure a condition.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

As used herein, the expression "biological target" refers to an organ, tissue and/or cell of an organism and/or to the organism itself.

As used herein the term "immunogenic" refers to a substance that is able to elicit an immune response.

Preparation Method of the Invention

The invention provides a method for preparing an immunogenic composition, comprising the steps of: collecting tumor cells from a donor; preparing a composition comprising the tumor cells and a metal-based coordination complex; and exposing the composition to electromagnetic radiation to provide the immunogenic composition, wherein the immunogenic composition is effective to elicit an immune response to the antigenic material in a patient to whom the immunogenic composition is administered, and the metal-based coordination complex is represented by one of formulas (I), (VI), (VIIa) or (II) above.

The tumor cells can comprise some or all of a tumor from a donor. Tumor cells express a whole array of tumor associated antigens (TAAs) that are both characterized and uncharacterized, and this rich source of antigens contains epitopes of both CD8+ cytotoxic T cells (CTLs) and CD4+ T helper cells. This is important, as the parallel presentation of both MEW Class I and II restricted antigens would help to generate a stronger overall anti-tumor response and long term CD8+ T cell memory via CD4+ T cell help (Toes R E, Ossendorp F, Offringa R, Melief C J. CD4 T cells and their role in antitumor immune responses. J Exp Med. 1999; 189:753-6). In addition, it could greatly diminish the chance of tumor escape compared to using single epitope vaccines. Furthermore, the use of whole tumor cells theoretically eliminates the need to define, test and select for immunodominant epitopes.

In the case of an autologous transplantation of tumor cells, the donor is the patient. It is also within the scope of the invention to transplant tumor cells from a donor who is not the patient, with a syngeneic transplant being most preferred when the transplantation is not autologous.

The major drawback for using autologous tumor cells is that they are only useful in single patient-tailored anti-tumor immunotherapies, and they could pose problems of collection, processing, reproducibility and inter-patient variability. Nevertheless, tumor cells from each patient potentially carry gene mutations encoding for unique TAAs that are important in stimulating effective and long-lasting anti-tumor responses. On the other hand, allogeneic tumor cell lines that share one or even several of the TAAs as autologous tumor cells provide a simpler method of delivering antigens in tumor immunotherapy. Allogeneic cell lines can be propagated in large quantities in cell factories and the quality can be easily assessed and monitored in good manufacturing practice (GMP) facilities.

The tumor cells are combined with a metal-based coordination complex, which is activated by electromagnetic radiation to deactivate the tumor cells prior to implantation in the patient. Preferably, the metal-based coordination complex is a PDC that is photoactivated so as to generate reactive oxygen species. Photoactivation can be achieved by the application of light from a light source. Suitable light sources include but are not limited to lasers, light emitting diodes, fiber optics and lamps.

In certain embodiments, the metal-based coordination complex can be activated by ionizing radiation in accordance with the teachings of U.S. Application 62/325,226, filed Apr. 20, 2016. The ionizing radiation is preferably at least one of X-rays and Gamma rays.

PDT dose parameters can be determined by a person of ordinary skill in the art with an understanding of the dosimetric and biological factors that govern therapeutic variability. See, e.g., Rizvi et al. "PDT Dose Parameters Impact Tumoricidal Durability and Cell Death Pathways in a 3D Ovarian Cancer Model." Photochemistry and photobiology. 2013; 89(4):942-952.

Factors to be considered include but are not limited to the amount of the PDC at the target site, tissue oxygenation, the molar extinction coefficient of the PDC at a chosen wavelength of light to produce a maximum level of reactive oxygen species, target (e.g. tumor) localization, size, shape, vascular structure, etc. The following table lists PDT parameters to be adjusted and provides preferred, non-exhaustive, values for said parameters.

| PDT Parameter | Value |
| --- | --- |
| Wavelength (nm) | 200-1000 or 400-950 or 500-950 |
| Fluence (J/cm$^2$) | 0.01 to 100,000 or 1 to 10,000 or 10 to 1,000 |
| Irradiance (mW/cm$^2$) | 10 to 10,000 or 50 to 5,000 or 100 to 1,000 |
| Irradiation Time (secs) | 1 to 10,000 or 10 to 5,000 or 100 to 1,000 |

Activation of the metal-based coordination complex to deactivate the tumor cells is preferably conducted extracorporeally.

The metal-based coordination complex is preferably at least one such compound disclosed in WO 2013158550 A1, WO 2014145428 A2, U.S. Pat. Nos. 6,962,910, 7,612,057, 8,445,475, 8,148,360 or US 20160206653 A1.

The metal of the metal-based coordination complex is at least one transition metal, which is preferably a Group 8 or 9 metal and is most preferably at least one of Ru, Rh, Os and Ir.

In certain embodiments, the metal-based coordination complex is combined with a metal-binding glycoprotein. Metal-binding glycoproteins suitable for use in the invention are capable of binding transition metals and delivering to a biological target said metals and other materials complexed with said metals. The metal-binding glycoproteins are preferably capable of binding Group 8 metals and/or Group 9 metals, and most preferably Ru, Os, Rh and Ir. Most preferred are the iron-binding glycoproteins transferrin, lactoferrin, ovotransferrin and melanotransferrin and variants thereof, with transferrin being most preferred. The glycoprotein can be purified from natural sources or can be from artificial sources. Thus, for example, the glycoprotein in certain embodiments is a recombinant transferrin, such as Apo-Transferrin or OPTIFERRIN, a recombinant human transferrin available from InVitria, a division of Ventria Bioscience. See US 20120088729 A1, Zhang et al., "Expression, purification, and characterization of recombinant human transferrin from rice (Oryza sativa L.)." Protein Expr Purif. 2010 November; 74(1):69-79. Epub 2010 May 4, and Steere et al., "Biochemical and structural characterization of recombinant human serum transferrin from rice (Oryza sativa L.)." J Inorg Biochem. 2012 Jul. 11; 116C:37-44. OPTIFERRIN is a particularly preferred glycoprotein as it increases the targeting and reduces the photobleaching of the metal-glycoprotein complexes of the invention.

Binding of Ruthenium, Ruthenium-Rhodium and Osmium-based photosensitizers to transferrin will increase their preferential uptake by cancer cells.

The invention further encompasses the use of metal-glycoprotein complexes of the invention to enhance uptake by cells of metal-based pharmaceutical agents that are not light activated (e.g., RAPTA, NAMI, KP1019, RM-175).

In all of the embodiments provided herein, examples of suitable optional substituents are not intended to limit the scope of the claimed invention. The compounds of the invention may contain any of the substituents, or combinations of substituents, provided herein.

Treatment Method of the Invention

The invention provides a method for treating a tumor in a patient, said method comprising administering to the patient an immunogenic composition, which is preferably prepared as described above.

The immunogenic composition is preferably administered in a pharmaceutically acceptable dosage form. The dosage form can further comprise at least one of diluents, extenders, carriers and the like. The dosage form is preferably a liquid, solid, gel or combination thereof. Suitable dosage forms include but are not limited to pills, tablets, capsules, eye drops and injectable liquids. The dosage form can be administered orally, rectally, topically, parenterally or intravenously. Administration can be systemic or localized (e.g., by injection into a tumor).

Some or all of the metal-based coordination complex can optionally be removed from the immunogenic composition prior implantation in the patient.

In certain embodiments, the immunogenic composition can further comprise at least one adjuvant to enhance the immune response. Suitable adjuvants include but are not limited to Transferrin binding proteins A and B, GMCSF expressing tumor cells lethally irradiated, Low dose cyclophosphamide (deplete Tregs), CpG oligodeoxyneucleotide (TLR9), Recombinant calreticulin, ATRA (all trans retinoic acid) (induces maturation of MDSC's), DBPMAF (serum vitamin D3-binding protein-derived macrophage activating factor), TNF-a, G-CSF (stimulate neutrophil), Γ-innulin (classical complement activator), Penicillin killed streptococci, Mycobacterium cell wall extract, BCG (live mycobacterial vaccine), Cryptosporidium parvam, Glycated Chitosan (polysaccharide preparation), Schizophyllan (Fungal β-glucan), Zymosan (yeast cell wall extract), Imiquimod (small molecule TLR-7 agonist) and immune check point blockers.

Immunogenic Composition of the Invention

The invention also encompasses the immunogenic composition. The composition can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the composition described herein.

The preparation methods described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Biological targets of the invention are organisms, organs, tissues and/or cells amenable to immunotherapy. The targets are preferably hyperproliferating cells, such as cancer and non-malignant lesions. In certain embodiments, the targets are immune privileged. The invention enables the treatment of targets across the blood-brain, blood-retina and blood-cerebrospinal fluid barriers.

The invention will be illustrated in more detail with reference to the following Examples, but it should be understood that the present invention is not deemed to be limited thereto.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

Our initial experiments provide encouraging results for tumor antigen vaccination approaches. Obviously, because tumor cells express a large load of "self" antigens and are selected to induce immune tolerance, methods to prepare whole tumor antigen become critically important to produce immunogenic vaccines.

We believe that PDT may act as an immunomodulatory approach. In our current work we developed the idea to mimic the in vivo PDT process in vitro by employing extracorporeal PDT to injure or kill syngeneic or autologous mammalian patient tumour cells. PDT treatment enhances stress on cells to induce expression of various immune stimulants/damage associated molecular patterns (DAMPs) like heat shock proteins (Hsp), extracellular ATP, and HMGB-1. In presence of these DAPMs, tumor antigens will be efficiently cross-presented to induce anti-tumor immune response. Oxidation of protein antigens allow protein unfolding and enhance both processing and exposure of immunogenic epitopes to specific T cells (Immunology. 1998 November; 95(3):314-21).

Whole tumor cells are a very simple approach to vaccination and can potentially be administered directly, without the need for dendritic cells (DCs). However, it is possible that we will use our extracorporeally treated injured or dead cells (including apoptotic and/or necrotic cells and/or their components, such as lysates, debris, endosomes, peptides, proteins, etc.) to stimulate antigen-presenting cells (DCs and macrophages) in vitro.

Live tumors cells are poorly immunogenic and have been shown to secrete soluble factors: vascular endothelial growth factor to suppress DCs differentiation and maturation, soluble Fas ligand to induce lymphocyte apoptosis, soluble MICA products to inhibit NKG2D-mediated killing by immune cells. In addition, IL-10 and TGF-β released by tumor cells could inhibit DC and T cell functions. Galectin-1 and indoleamine 2,3-dioxygenase also inhibit T cell activation. A method to kill and at the same time to enhance the immunogenicity of tumor cells is therefore required. The question whether an apoptotic or necrotic cell is intrinsically immunogenic or tolerogenic, and indeed more suitable for use in immunotherapy, has long been debated. Furthermore, although some differences exist between purified apoptotic and necrotic cells, their equivalent ability to mature DCs phenotypically, as well as to elicit both effective immune priming and antitumor therapeutic efficacy in vivo when presented by DCs, has been demonstrated. DCs pulsed with apoptotic tumor cells have been used successfully to induce tumor vaccination. Immunogenic cell death is not a simple correlate of cell death type but depends on a large extent on the death-initiating stimulus that could cause the exposure of immunogenic factors on the cell surface or the release of immunogenic signals into the extracellular space. Some of the technical aspects used methods of preparing the whole tumor cell vaccines are discussed below.

Example 1

Rodent

Rat glioma (RG2) cells (ATCC CRL-2433) are cultured in DMEM media following ATCC recommendations.

TLD1433 (2 µM) and apo-transferrin (10 mg/mL) were diluted in pre-warmed DMEM. DMEM was removed from attached RG2 cells and TLD1433/apo-transferrin mixture was added, covering all the cells. RG2 cells were incubated with TLD1433/apo-transferrin mixture for four hours. After four hours, TLD1433/apo-transferrin mixture was removed from the RG2 cells. RG2 cells were detached and re-suspended in pre-warmed PSB at a concentration of $10^7$ cells/mL. RG2 cells were exposed to 525 nm light to a total energy density of 90 J cm$^{-2}$. RG2 cells were collected and stored in a refrigerator for rat injection on the same day or at −80° C. for long term storage. Rats were prepared and anesthetized for surgery according to UHN animal facility protocol. 0.5 mL (total 5×10$^6$ cells) of extracorporeal treated RG2 were injected subcutaneously into the back of the rat.

Example 2

Human (Prophetic)

Tumor biopsy samples will be used to prepare PDT treated tumor cells vaccines. A single cell suspension of whole tumor mass is prepared by enzymatic digestion with collagenase D or by mechanical disruption. The single cell suspension will be put into suitable media with 2 uM TLD1433 and 10 mg/ml human apo-transferrin. Cells will then be incubated for 4 hours. After 4 hours, the cells will be spun down and washed with PBS. Finally, cells will be suspended in PBS at 10×10$^6$ cells/ml concentration. This suspension will be placed in a sterile 3.5 mm diameter tissue culture dish. Then these cells will be irradiated with 525 nm wavelength green light at 90 J/cm$^2$. The immunogenic composition comprising a mixture of apoptotic, necrotic and DAMPs will be intramuscularly injected in to same patients. We expect that this PDT treated vaccine will be a strong therapeutic vaccine to induce robust anti-tumor immune response and also antigen spread by identifying new tumor antigens.

Example 3

Dendritic Cell Vaccine in Rat Model (Prophetic)

Dendritic cells (DCs) are prepared using syngeneic Fisher SAS rats. Bone marrow cells are collected from femora and tibiae of wild type Fischer rats. Single cell suspension is prepared by mechanical disruption on sterile nylon mesh. Red blood cells are lysed with ACK buffer. Remaining cells are plated with DC culture medium (DMEM plus 10% FCS, 20 ng/ml Rat-GM-CSF and 5 ng/ml rat-IL-4). On day 3, non-adherent granulocytes, T cells and B-cells are gently removed and replaced with fresh medium. Two days later (on Day 5), loosely adherent DCs are dislodged and re-plated in new plates. They are grown until day 7 and harvested as Immature DCs. They are characterized with different DC markers like CD11c, CD40, CD80, CD86 and pMHC class I and others.

These cells are activated and armed with extracorporeal PDT treated RG2 cells and other cytokines. RG2 cells grown to 80 to 90% confluence are incubated with a metal-based coordination complex of the invention. After 4 hrs, excess complex is washed off, and complexed cells are harvested and re-suspended in suitable media (RPMI or DMEM). Electromagnetic radiation is then applied to activate the metal-based coordination compounds to inactivate the RG2 cells.

The RG2 cells are co-cultured with DCs and grown for 24 to 48 hrs in suitable media. The DCs are then harvested and characterized for maturity with different DC markers. Upon confirming their activation status, they are used as DC vaccine.

DCs are administered in different doses to rats with RG2 glioblastoma as therapeutic vaccine. Multiple doses will be given based on requirements.

DCs can also be used as prophylactic vaccines. Tumor-free rats vaccinated with the DCs are challenged with tumor cell injections 7 to 14 days post-vaccination and will survive substantially longer than control group rats.

DC vaccines are not limited to glioblastoma multiforme or use in rats, as shown by the following examples.

Example 4

Dendritic Cell Vaccine in Human Model (Prophetic)

Leukopheresis monocytes are separated from human cancer patients. They are grown to differentiate into DCs with a cocktail of cytokines. Differentiated DCs are characterized by different DC markers. Upon confirming the expression, those cells are co-incubated with PDT-treated tumor cells from the same patient. Upon co-culture, the DCs will present tumor antigens on HLA molecules. These armed DCs are then transferred back to the same patient as a cancer vaccine. This infusion of DCs could be through various routes at different doses and different time points.

Example 5

Adoptive T Cell Therapy in a Rat Model

The tumor cell stimulated DCs of Examples 3 and 4 can be used as activators of tumor specific T cells. DC vaccine prepared in Examples 3 and 4 is used to in-vitro stimulate tumor specific T cells for the same patient. The source of the T cells is tumor tissue (Tumor infiltrated lymphocytes) or from peripheral blood. T cells are co-cultured with PDT treated tumor cell stimulated DCs along with a cytokine cocktail. Once these cells are strongly stimulated and expanded, they are reintroduced into the same patient to fight against primary tumor and possible metastatic lesions. They will also lead to memory response to protect the patient from possible relapse of the same tumor or tumors with shared tumor antigens.

Activated DCs are prepared as in Example 3. A syngeneic Fischer rat is used to prepare T cells. A single cell suspension is prepared from the spleen of a naïve Fisher rat. Red blood cells are lysed with ACK buffer. CD8 T cells are isolated from remaining cells by using negative selection using CD8 T cell isolation kits. Isolated CD8 T cells are co-cultured with activated DCs for 3 to 8 days. These expanded cells are transferred to a rat with RG2 tumor. T cell transfer is done once or multiple times. The animal is monitored for protection from this adoptive T cell therapy.

Example 6

Adoptive T Cell Therapy in a Human Model

Activated DCs are prepared as in Example 4. CD8 T cells are separated from tumor infiltrated T cells, after a tumor is surgically excised. CD8 T cells could also be separated by leukopheresis. The CD8 T cells are grown in the presence of activated DCs along with cocktail of cytokines. Later, activated and expanded CD8 T cells are reintroduced into the same patient to treat cancer.

While the invention has been described in detail and with reference to specific examples thereof, it will be apparent to one skilled in the art that various changes and modifications can be made therein without departing from the spirit and scope thereof.

What is claimed is:

1. A method for treating a tumor in a patient, said method comprising:
   administering to the patient an immunogenic composition comprising antigenic material inactivated by treatment with a metal-based coordination complex and electromagnetic radiation,
   wherein the immunogenic composition is effective to elicit an immune response to the antigenic material in the patient after administration and the metal-based coordination complex is represented by one of the following formulas:
   (a) formula (I):

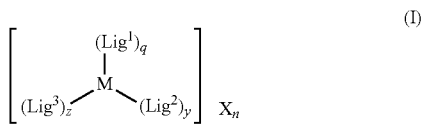

including hydrates, solvates, pharmaceutically acceptable salts, prodrugs and complexes thereof, wherein:
M at each occurrence is independently selected from the group consisting of osmium, ruthenium and rhodium;
X is selected from the group consisting of $Cl^-$, $PF_6^-$, $Br^-$, $BF_4^-$, $ClO_4^-$, $CF_3SO_3^-$, and $SO_4^{-2}$;
n=0, 1, 2, 3, 4, or 5;
q is independently at each occurrence 0, 1, or 2;
y is independently at each occurrence 0, 1, or 2;
z is independently at each occurrence 1, 2, or 3;
$Lig^1$ is a bidentate ligand that at each occurrence is each independently selected from the group consisting of

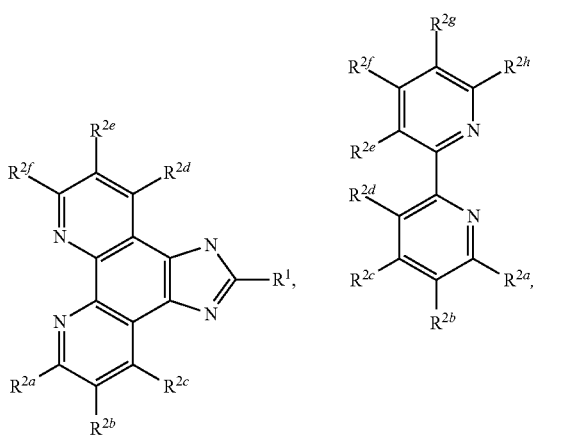

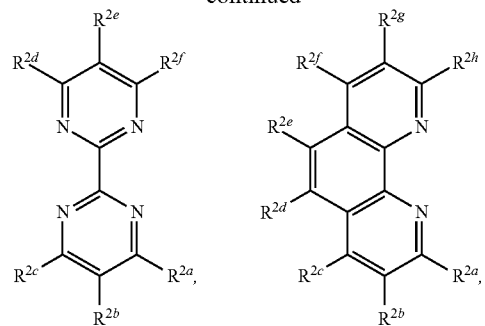

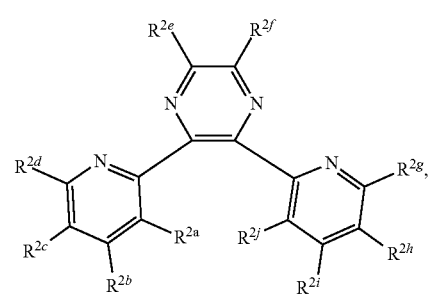

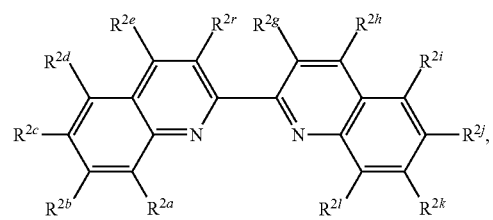

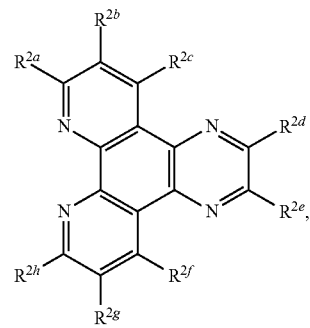

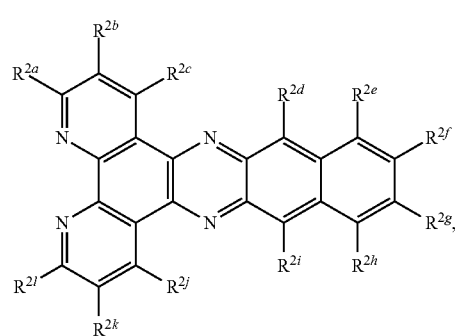

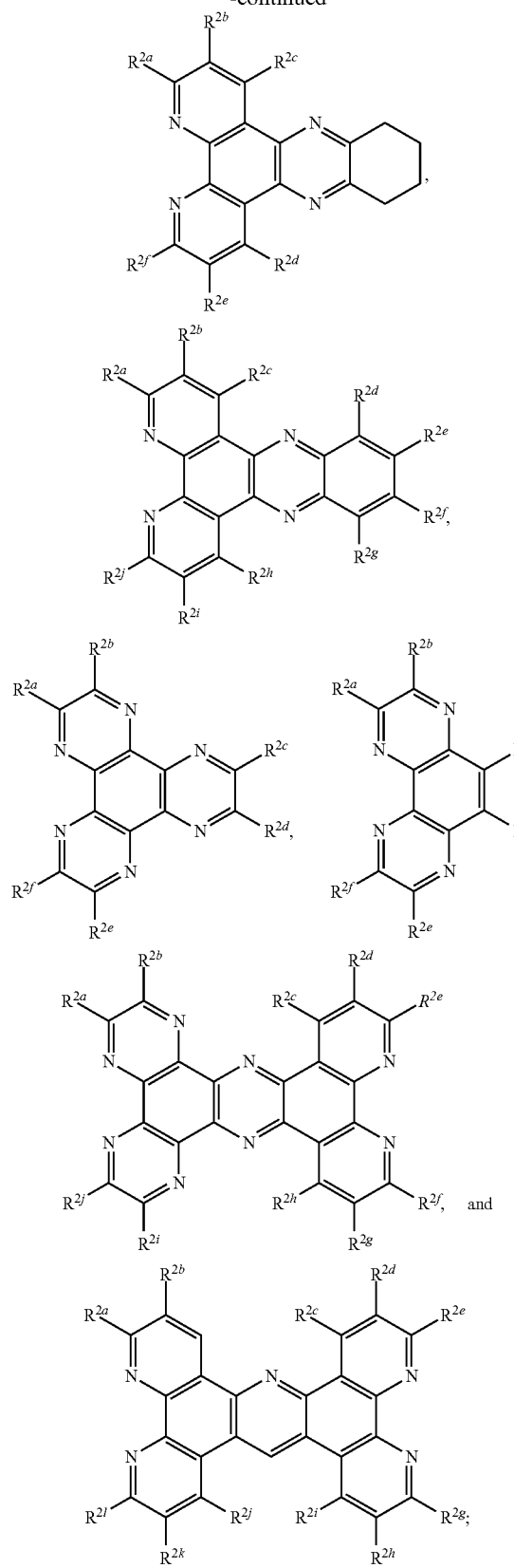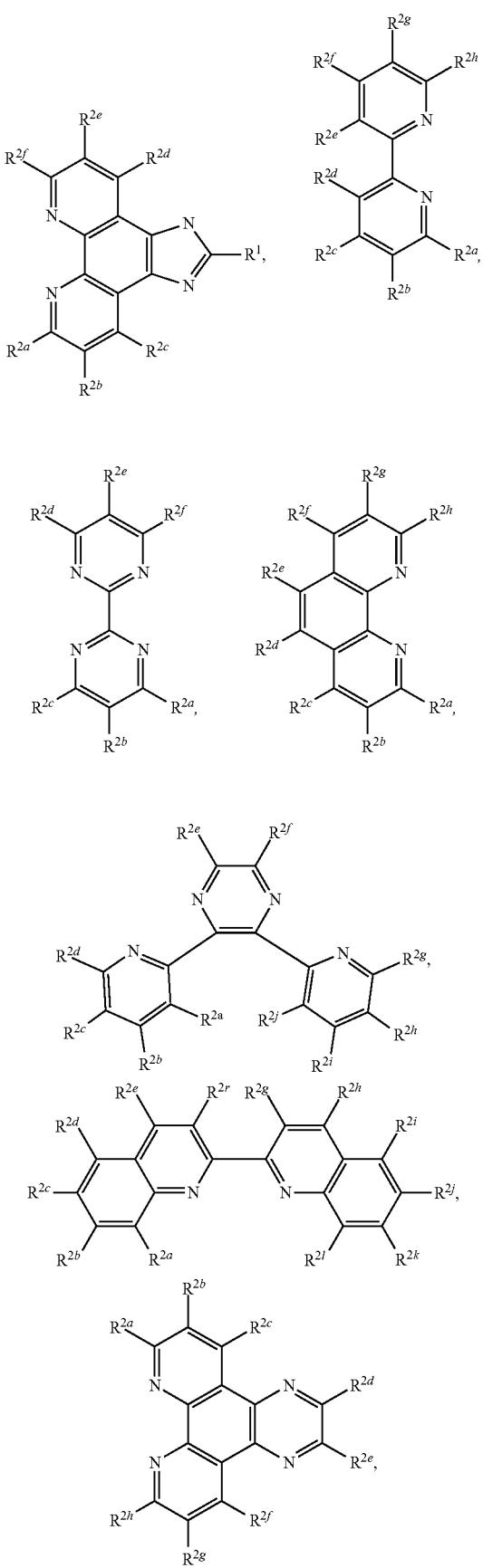
Lig² is a bidentate ligand that at each occurrence is each independently selected from the group consisting of -continued
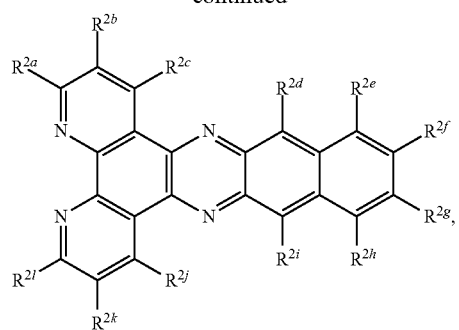
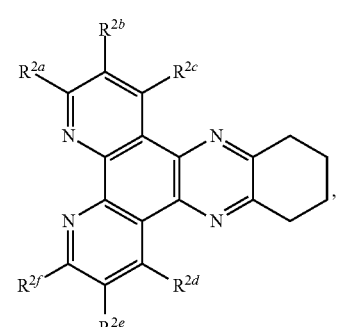
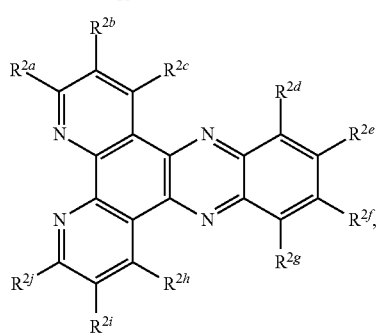
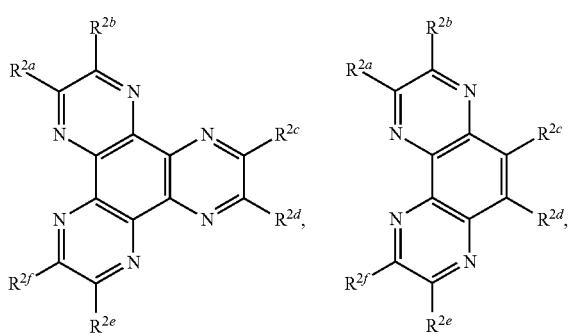
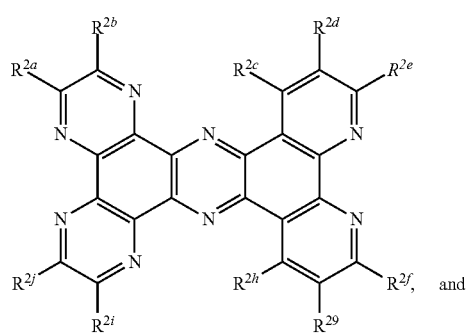
-continued
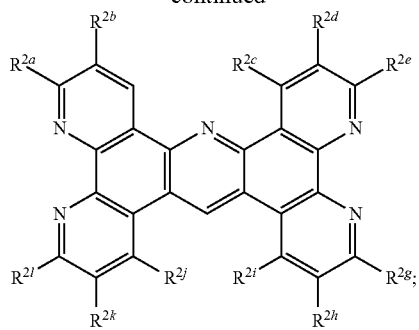
Lig³ is a bidentate ligand that at each occurrence is each independently selected from the group consisting of
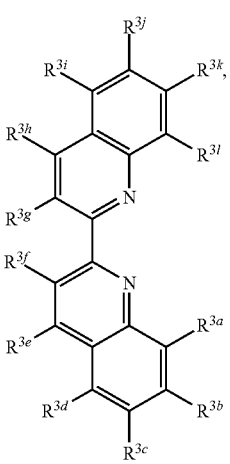
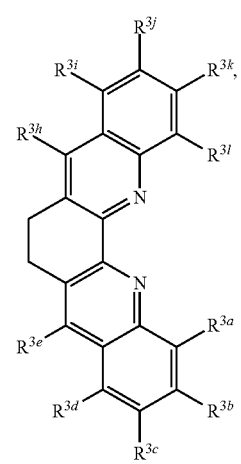
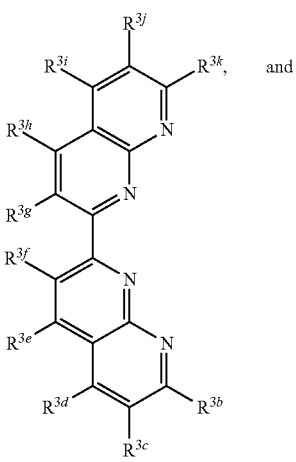
and

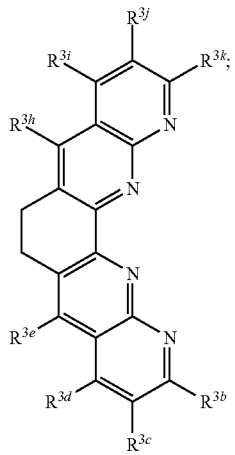
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
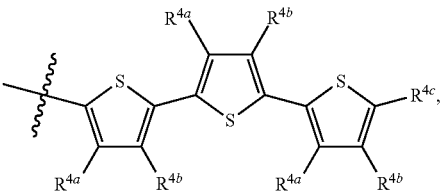
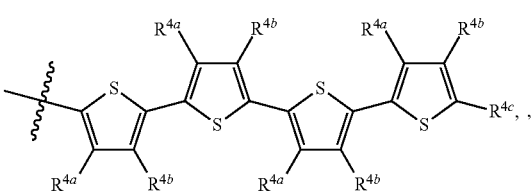
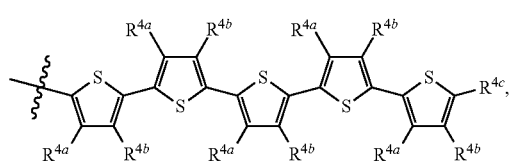
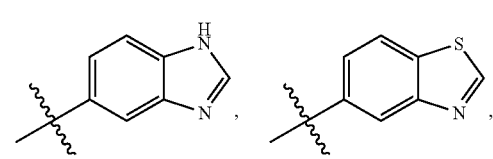
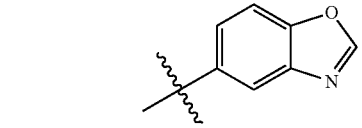
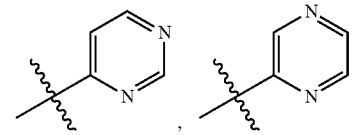
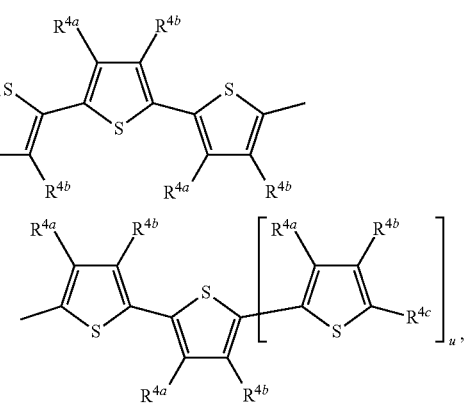
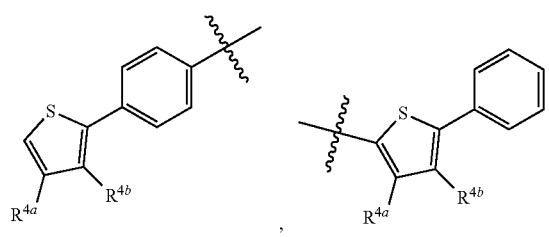
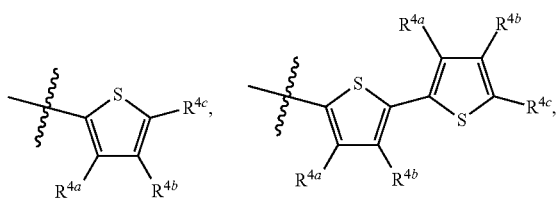
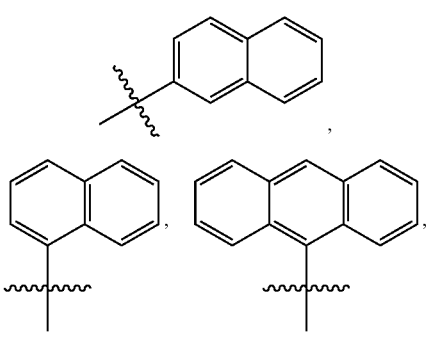

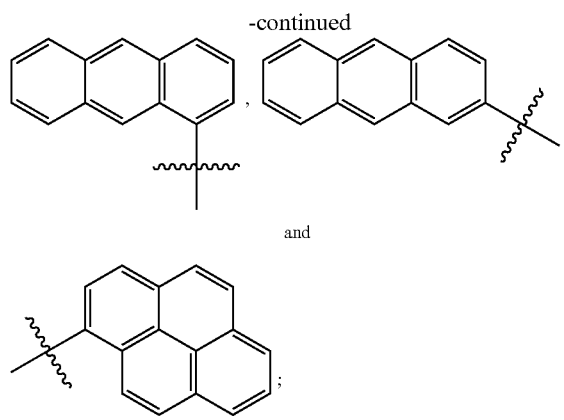

and

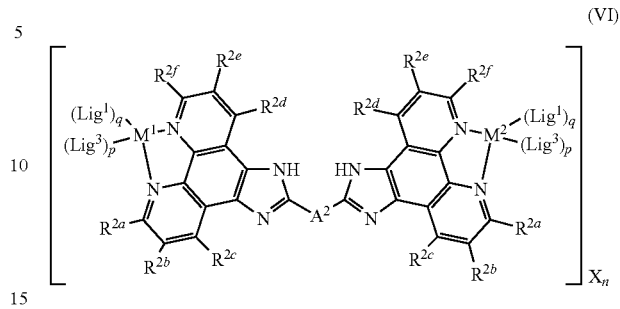

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl;

(b) formula (VI):

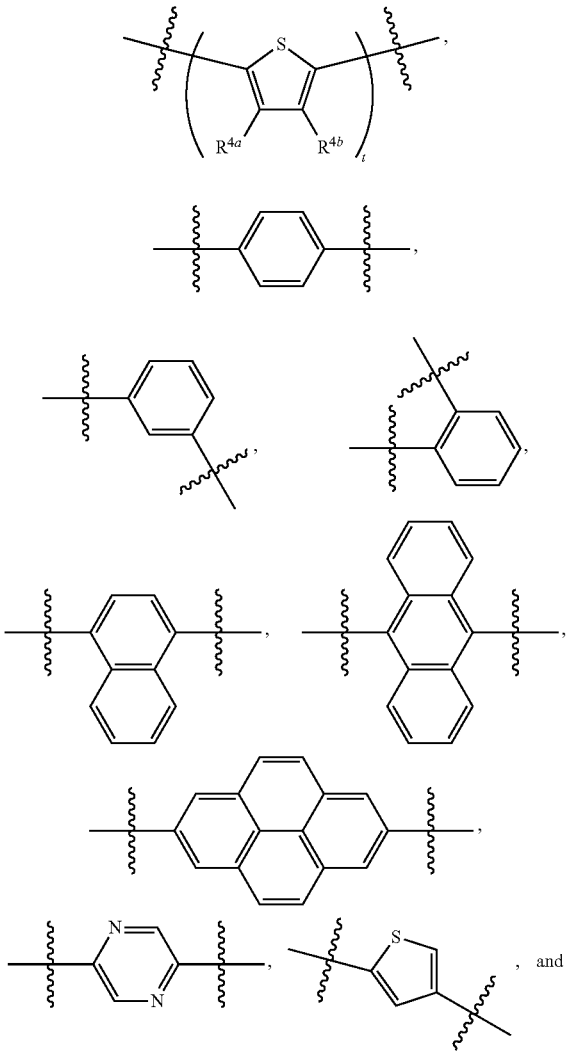

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

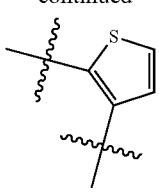
t is an integer;
(c) formula (VIIa):
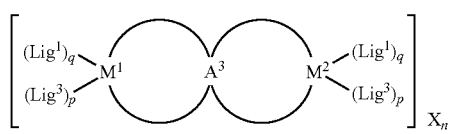
including hydrates, solvates, pharmaceutically acceptable salts, prodrugs and complexes thereof wherein:
$A^3$ is selected from the group consisting of
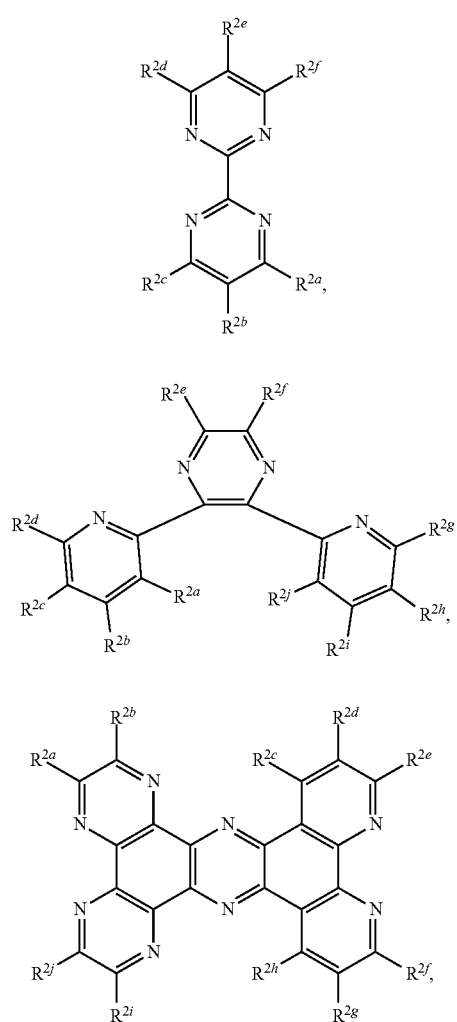
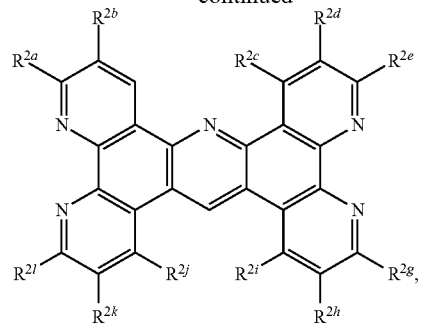
and
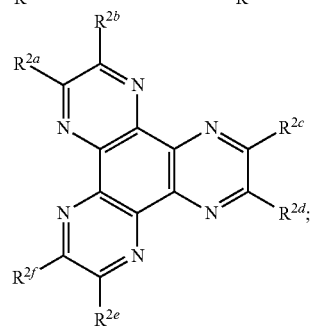
$Lig^1$ is a bidentate ligand that at each occurrence is each independently selected from the group consisting of
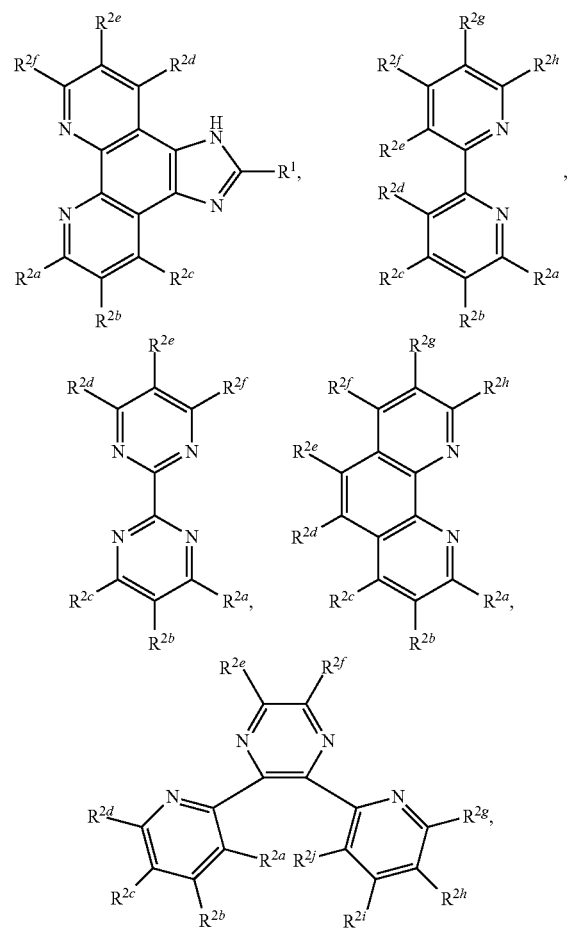

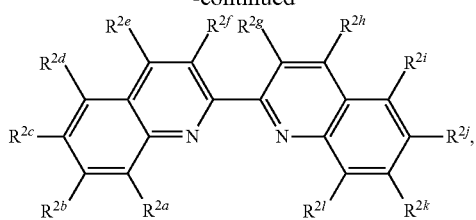
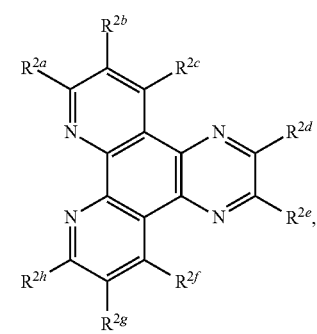
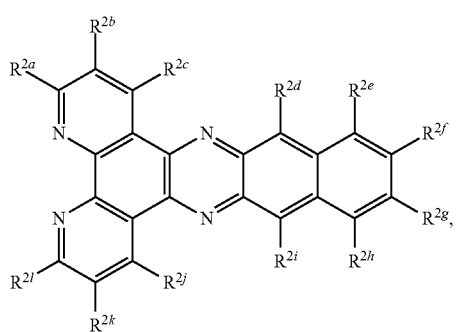
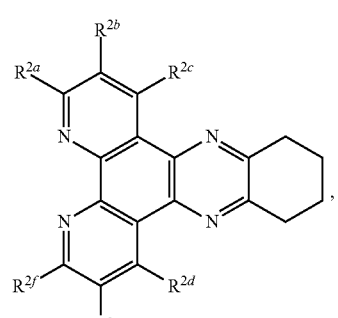
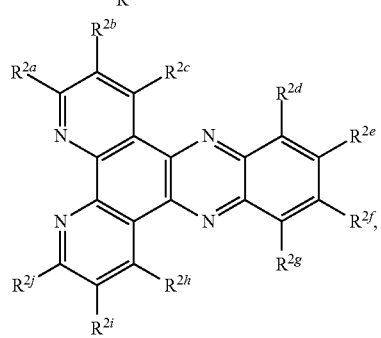
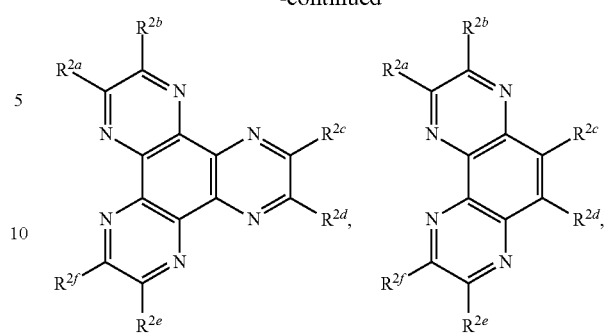
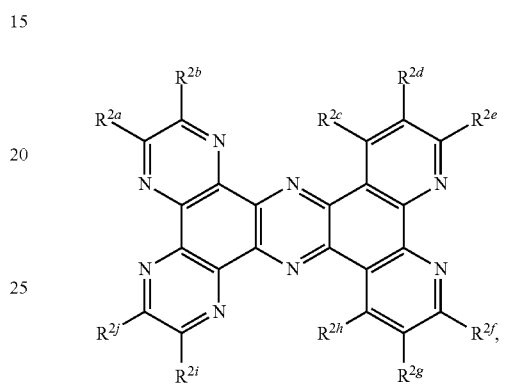
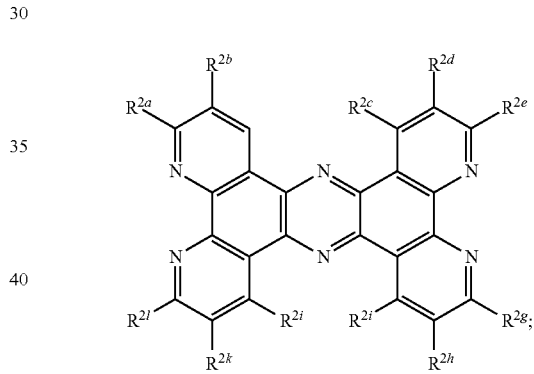
Lig$^3$ is a bidentate ligand that at each occurrence is each independently selected from the group consisting of
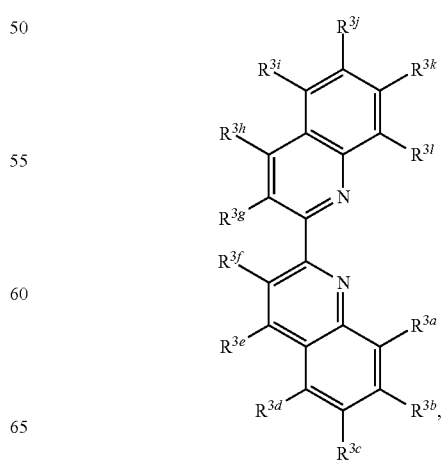

-continued
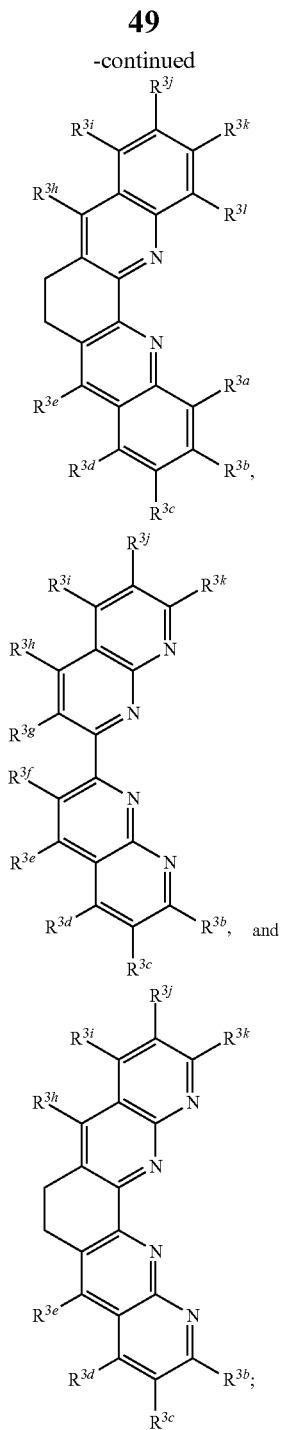
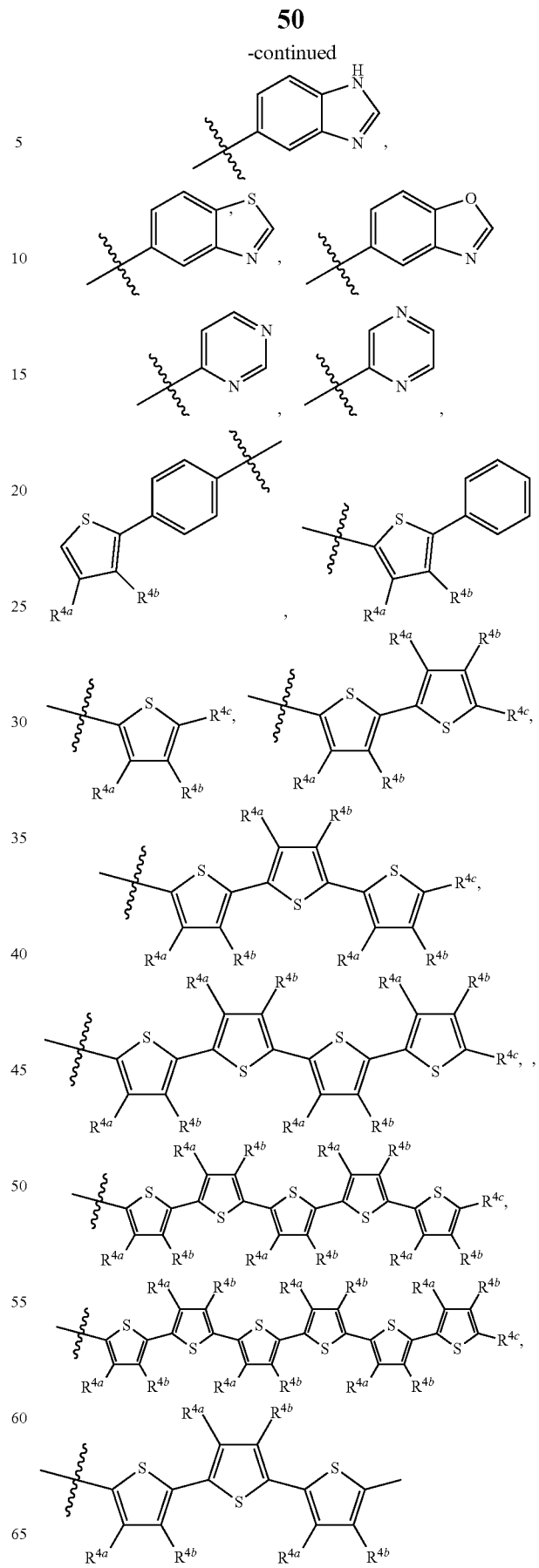
R[1] is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
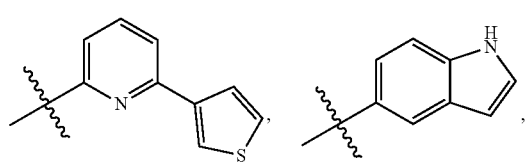

-continued

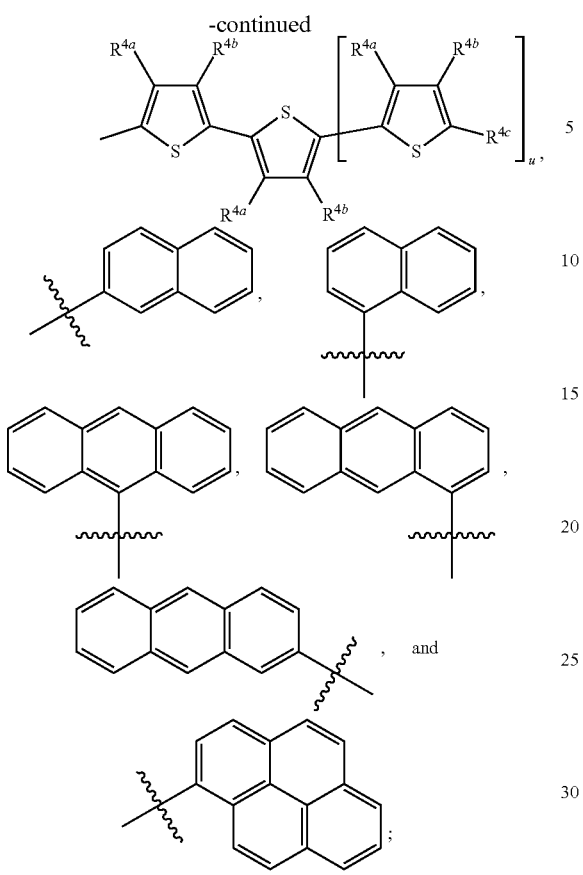

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl p is independently at each occurrence 0, 1, or 2;

q is independently at each occurrence 0, 1, or 2; and n is 0, 1, 2, 3, 4, or 5;

(d) formula (II):

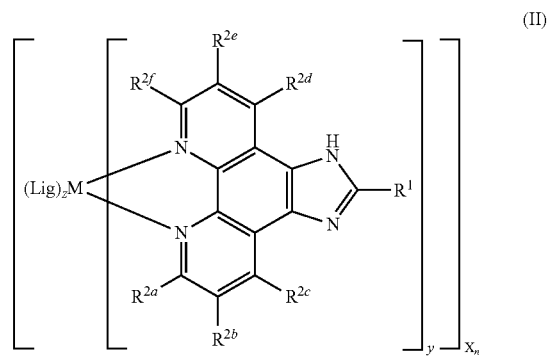

(II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

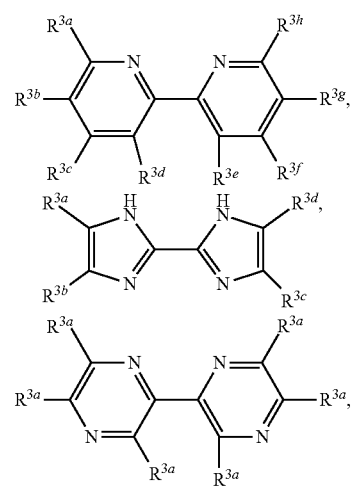

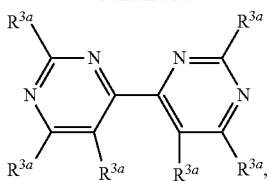
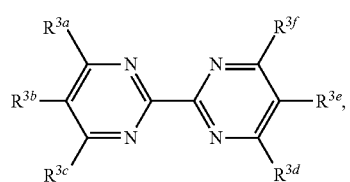
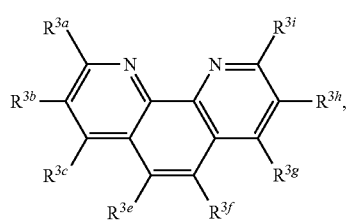
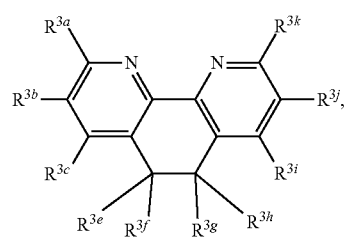
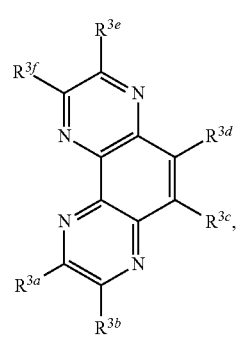
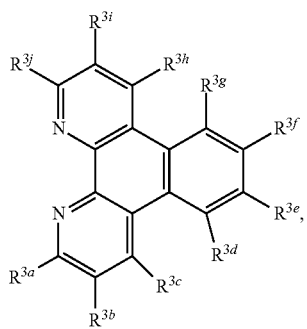
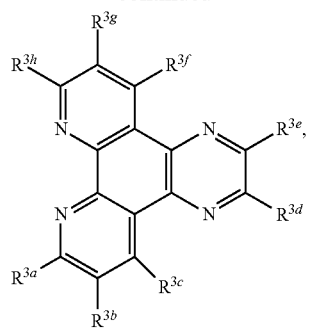
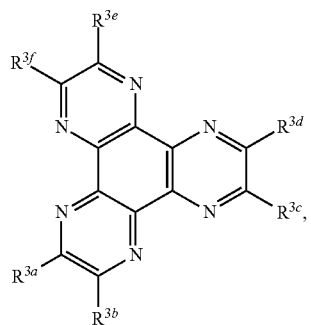
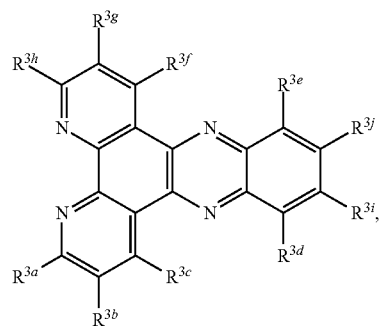
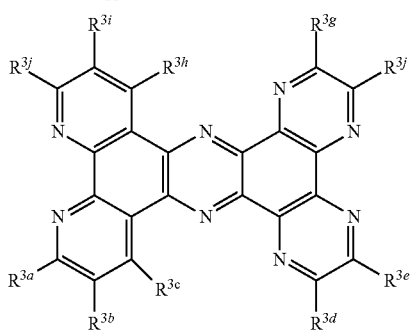
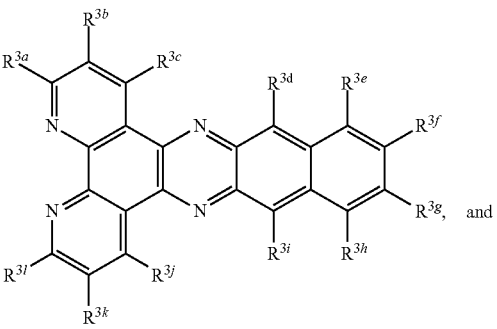

-continued

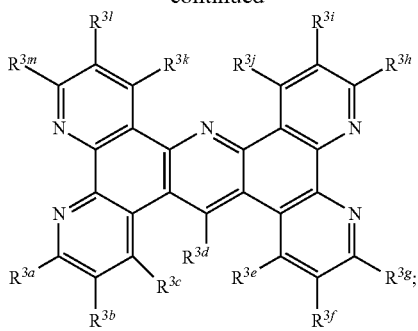

R[1] is selected from the group consisting of

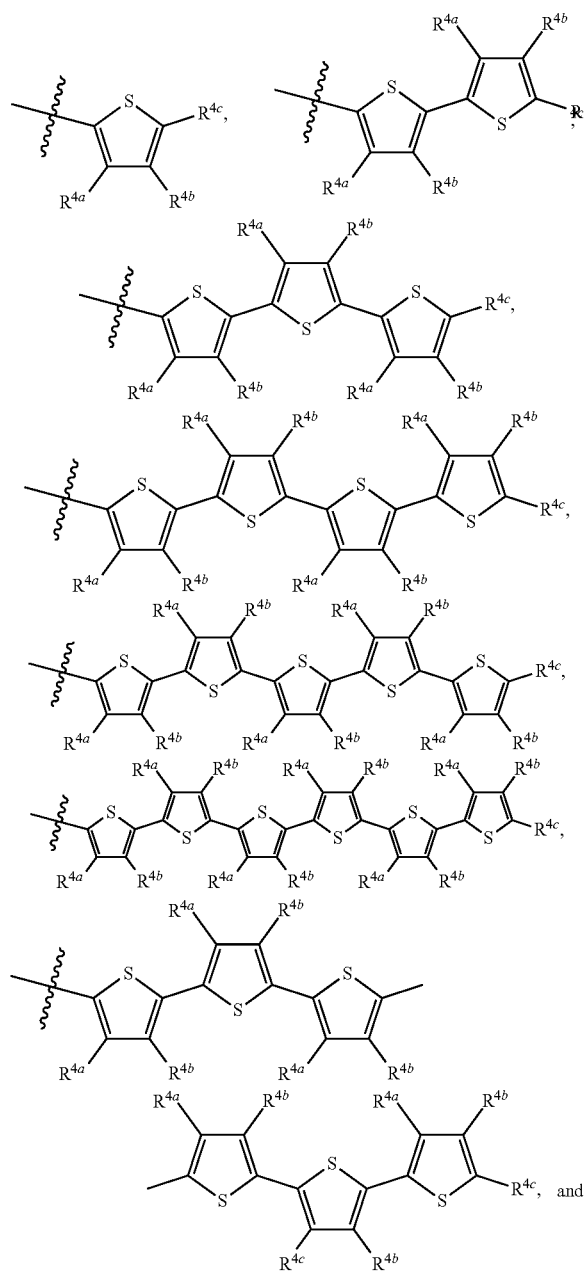

-continued

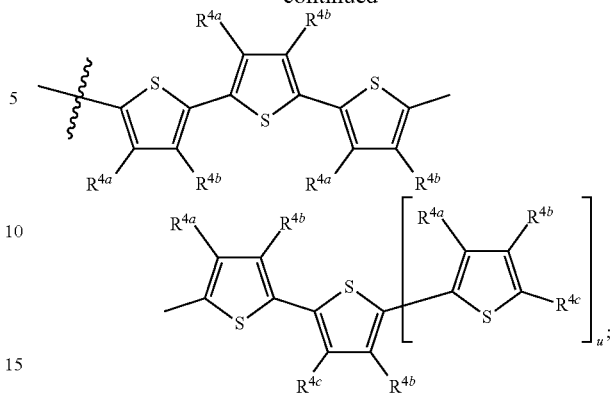

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

2. The method of claim 1, wherein the immunogenic composition is prepared by collecting tumor cells from a donor, preparing a composition comprising the tumor cells and the metal-based coordination complex, and exposing the composition to the electromagnetic radiation to provide the immunogenic composition.

3. The method of claim 2, wherein the electromagnetic radiation is laser light having a wavelength from 500-950 nm.

4. The method of claim 2, wherein the electromagnetic radiation is X-rays or Gamma rays.

5. The method of claim 2, wherein the donor is the patient and is a human, and the tumor cells are cancer cells.

6. The method of claim 2, wherein the metal-based coordination complex further comprises transferrin.

7. The method of claim 2, wherein M is at least one of Ru, Rh, Os and Ir.

8. The method of claim 2, wherein the metal-based coordination complex has the following structure:

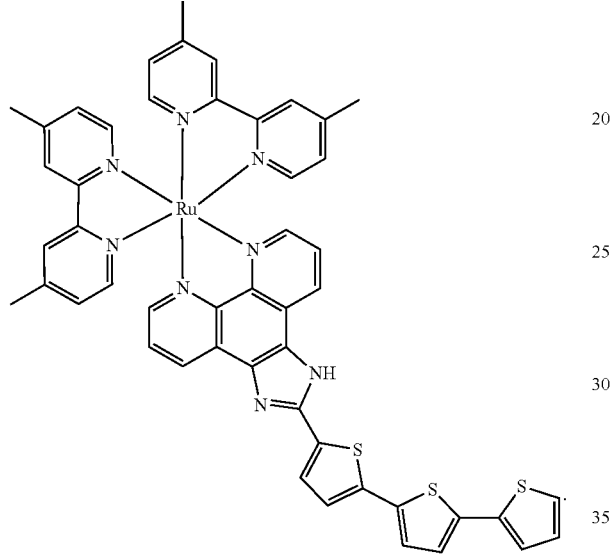

9. A method for preparing an immunogenic composition, said method comprising:
   collecting tumor cells from a donor;
   preparing a composition comprising the tumor cells and a metal-based coordination complex; and
   exposing the composition to electromagnetic radiation to provide the immunogenic composition,
   wherein the immunogenic composition is effective to elicit an immune response to the antigenic material in a patient to whom the immunogenic composition is administered, and the metal-based coordination complex is represented by one of the following formulas:
   (a) formula (I):

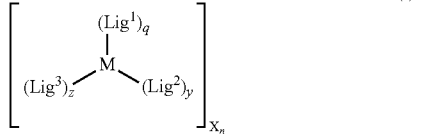

including hydrates, solvates, pharmaceutically acceptable salts, prodrugs and complexes thereof, wherein:

M at each occurrence is independently selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

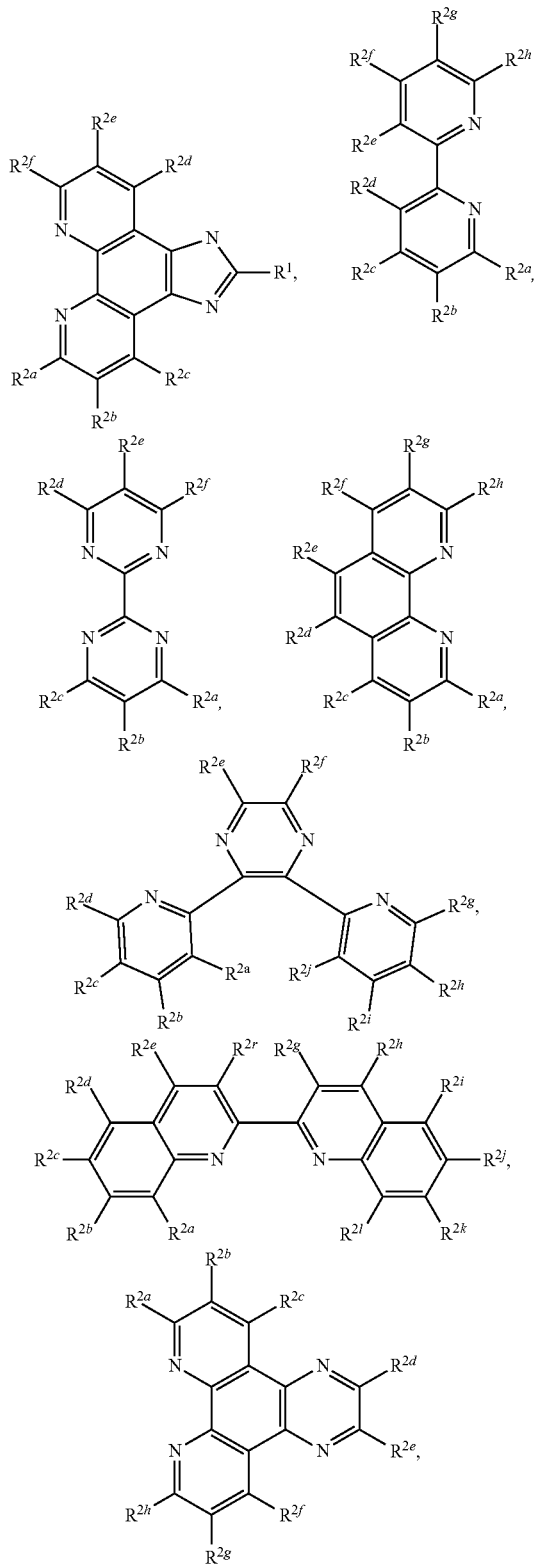

-continued
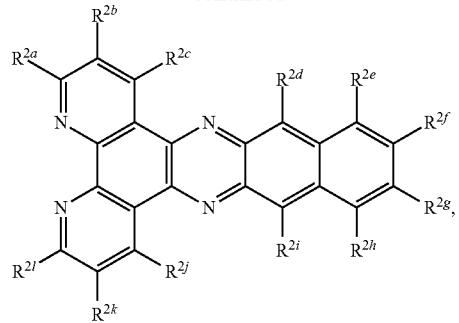
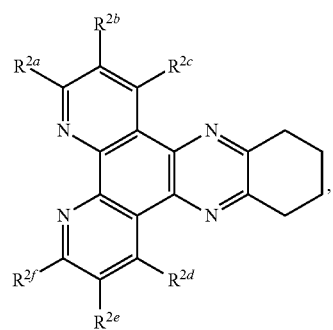
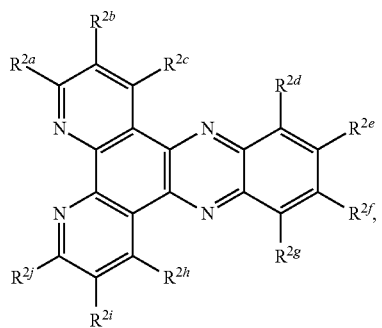
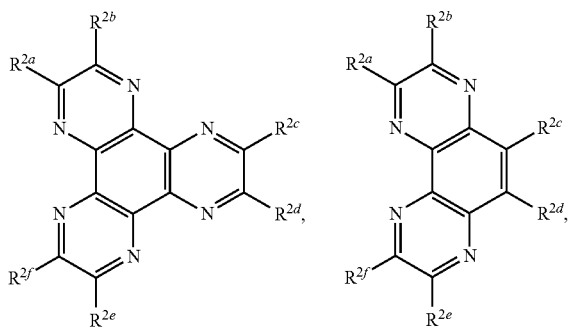
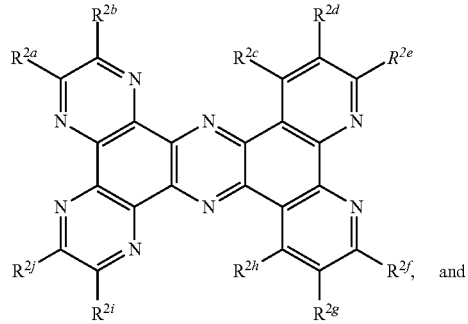
-continued
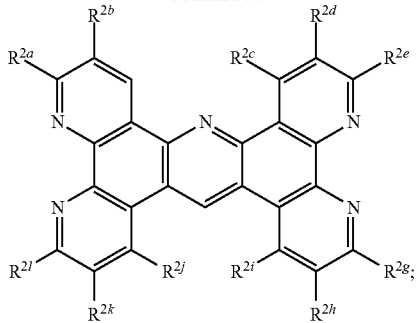
Lig² is a bidentate ligand that at each occurrence is each independently selected from the group consisting of
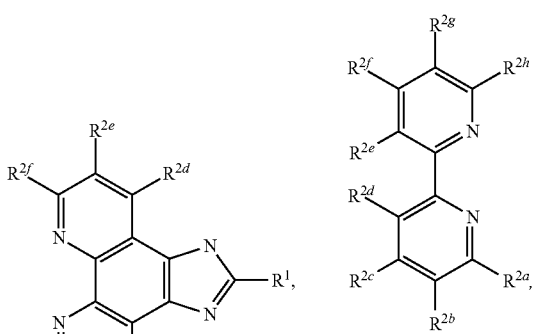
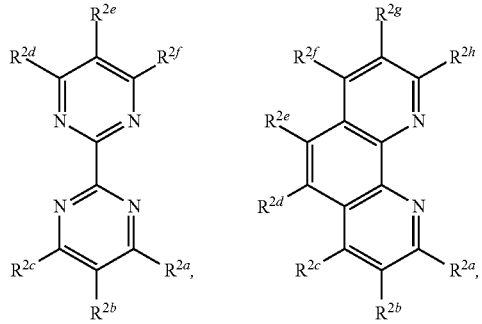
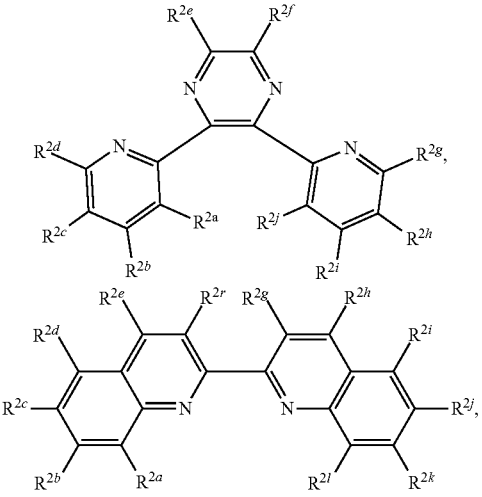

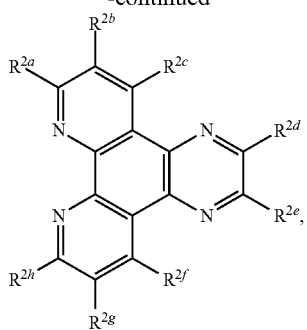
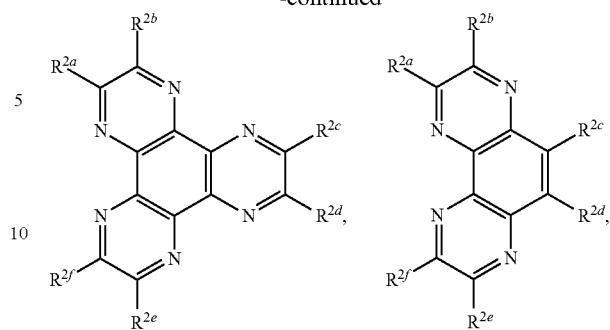
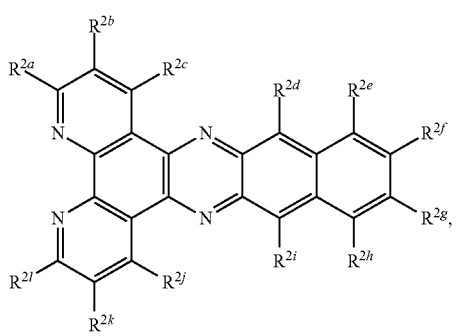
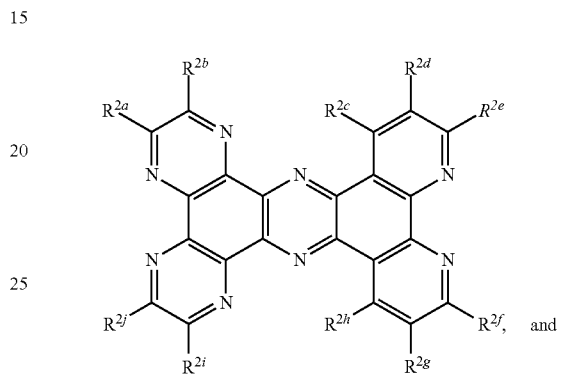
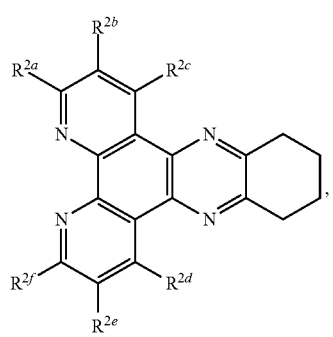
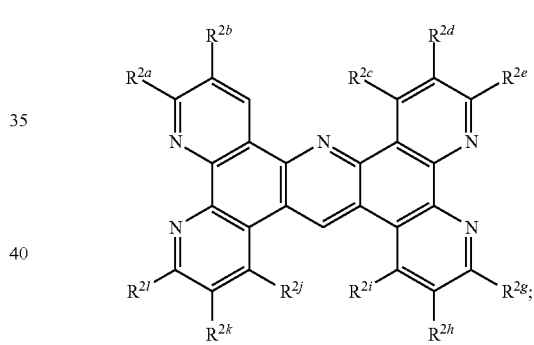
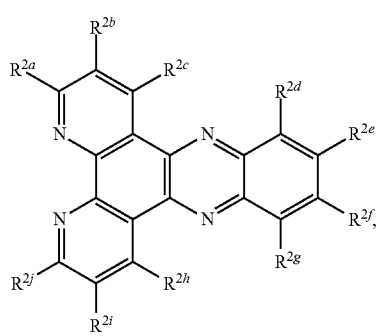
Lig³ is a bidentate ligand that at each occurrence is each independently selected from the group consisting of -continued
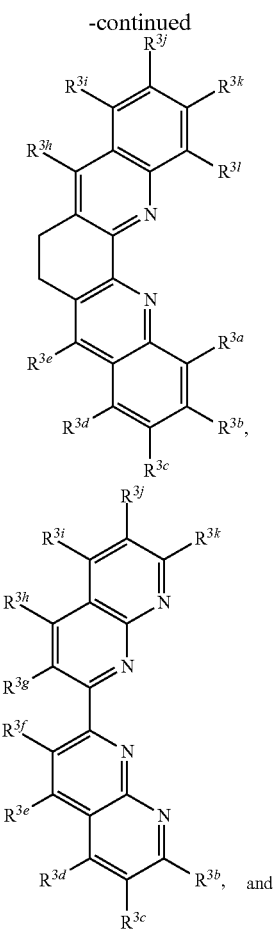
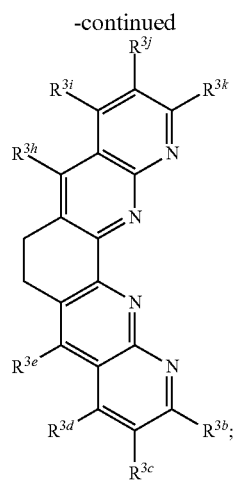
R[1] is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
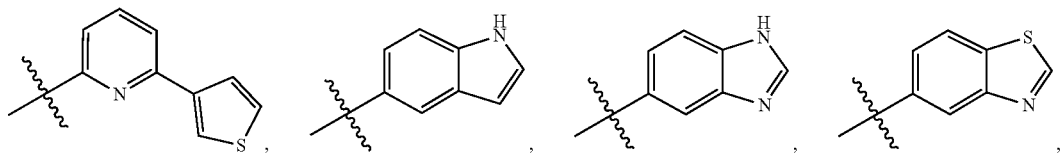
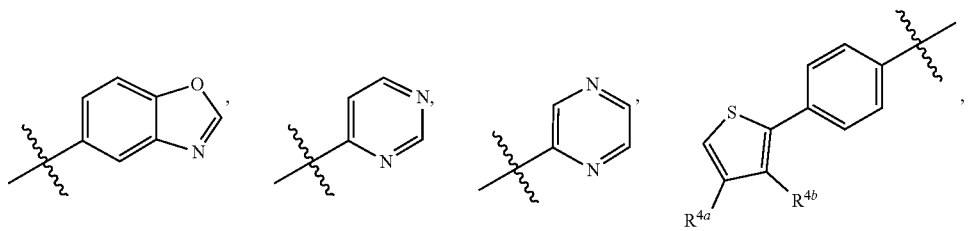
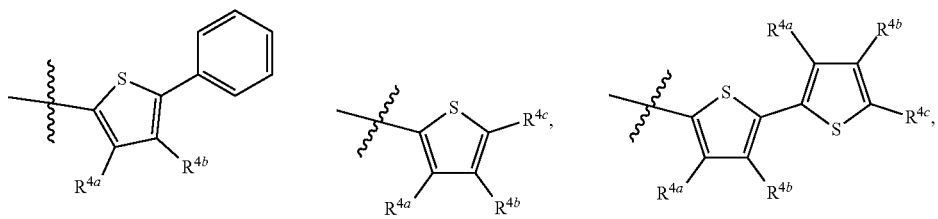

-continued

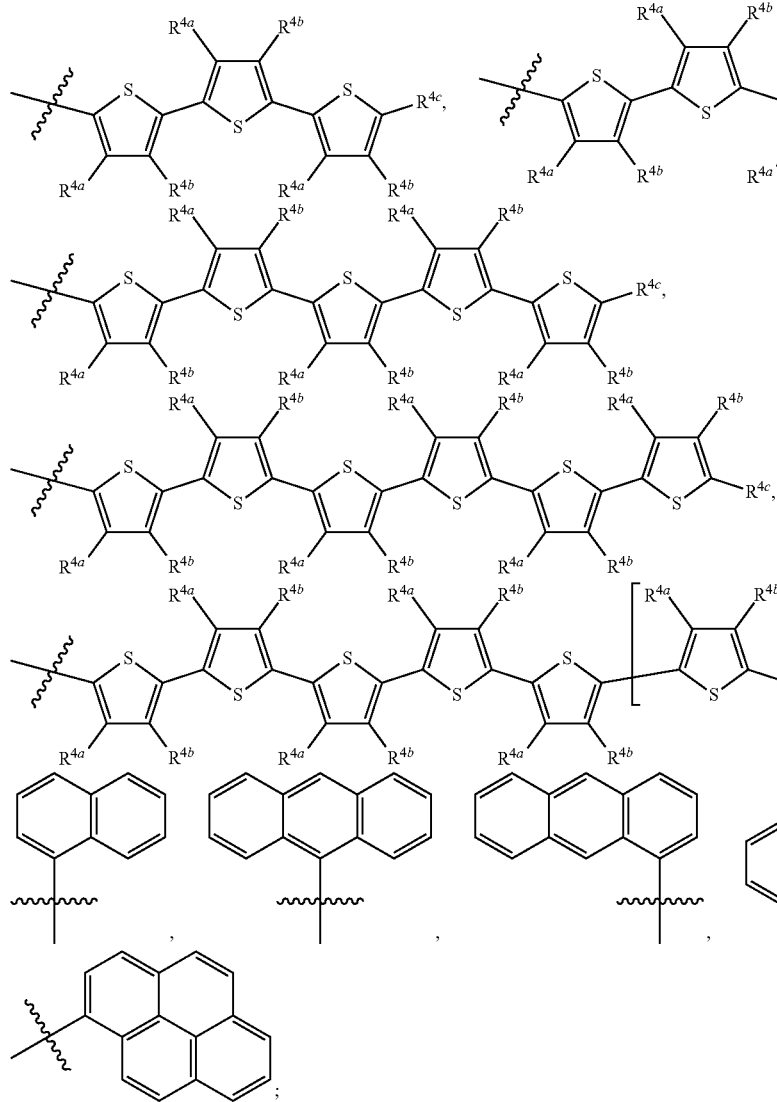

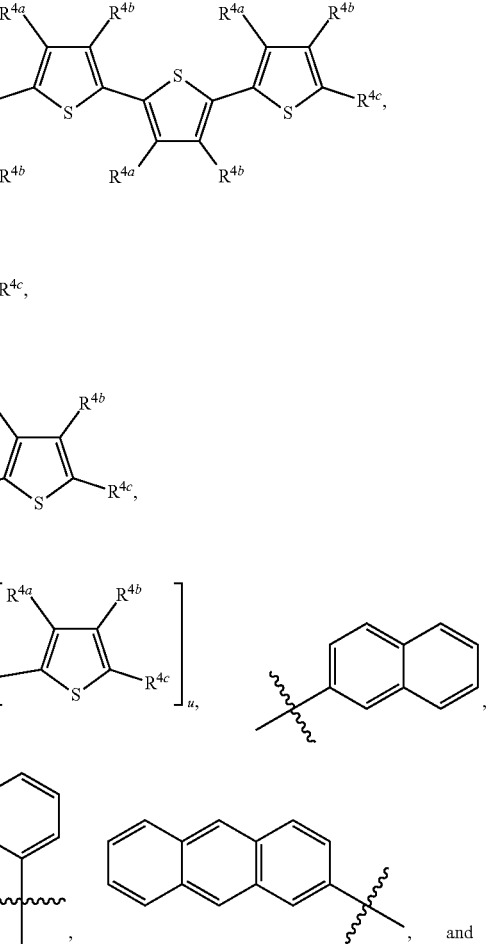

u is an integer;

R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, R$^{2k}$, and R$^{2l}$ at each occurrence are each independently selected from the group consisting of hydrogen, C$_{1-6}$ optionally substituted alkyl, C$_{1-6}$ optionally substituted branched alkyl, C$_{3-7}$ optionally substituted cycloalkyl, C$_{1-6}$ optionally substituted haloalkyl, C$_{1-6}$ optionally substituted alkoxy, CO$_2$R$^5$, CONR$^6_2$, NR$^7_2$, SO$_3$H, sulfate, sulfonate, optionally substituted aryl, optionally substituted aryloxy, optionally substituted heteroaryl, and optionally substituted heterocycle;

R$^{3a}$, R$^{3b}$, R$^{3c}$, R$^{3d}$, R$^{3e}$, R$^{3f}$, R$^{3g}$, R$^{3h}$ R$^{3i}$, R$^{3j}$, R$^{3k}$, and R$^{3l}$ at each occurrence are each independently selected from the group consisting of hydrogen, C$_{1-6}$ optionally substituted alkyl, C$_{1-6}$ optionally substituted branched alkyl, C$_{1-6}$ optionally substituted haloalkyl, C$_{1-6}$ optionally substituted alkoxy, optionally substituted phenyl, and CO$_2$R$^8$;

R$^{4a}$, R$^{4b}$, and R$^{4c}$ at each occurrence are each independently selected from the group consisting of hydrogen, C$_{1-6}$ optionally substituted alkyl, C$_{1-6}$ optionally substituted branched alkyl, C$_{1-6}$ optionally substituted cycloalkyl, C$_{1-6}$ optionally substituted haloalkyl, C$_{1-6}$ optionally substituted alkoxy, CO$_2$R$^5$, CONR$^6_2$, NR$^7_2$, sulfate, sulfonate, optionally substituted aryl, optionally substituted aryloxy, optionally substituted heteroaryl, and optionally substituted heterocycle;

R$^{4a}$ and R$^{4b}$ at each occurrence on a thiophene ring are taken together with the atom to which they are bound to form an optionally substituted ring having from 6 ring atoms containing 2 oxygen atoms;

R$^5$ at each occurrence are each independently selected from the group consisting of hydrogen and optionally substituted alkyl;

R$^6$ at each occurrence are each independently selected from the group consisting of hydrogen and optionally substituted alkyl;

R$^7$ at each occurrence are each independently selected from the group consisting of hydrogen and optionally substituted alkyl; and R$^8$ at each occurrence are each independently selected from the group consisting of hydrogen and optionally substituted alkyl;

(b) formula (VI):

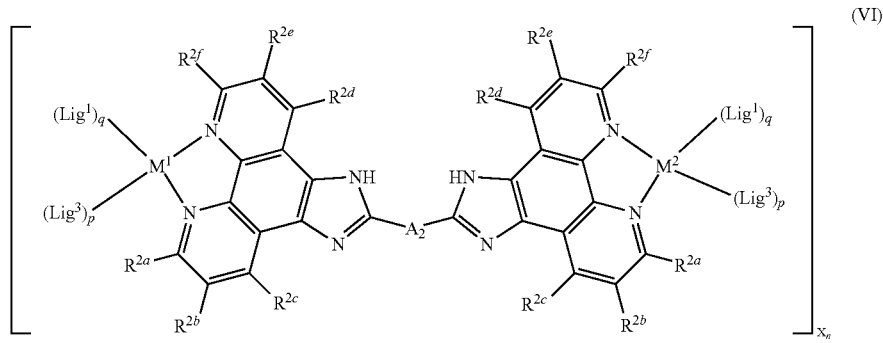

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

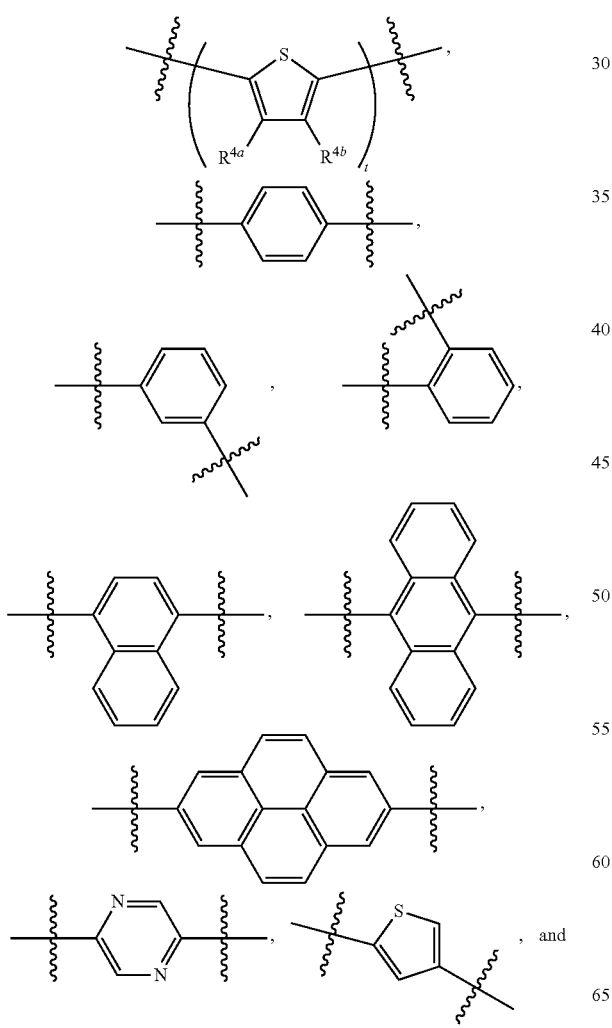

, and

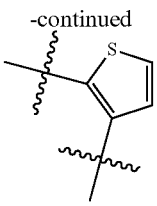

t is an integer;

(c) formula (VIIa):

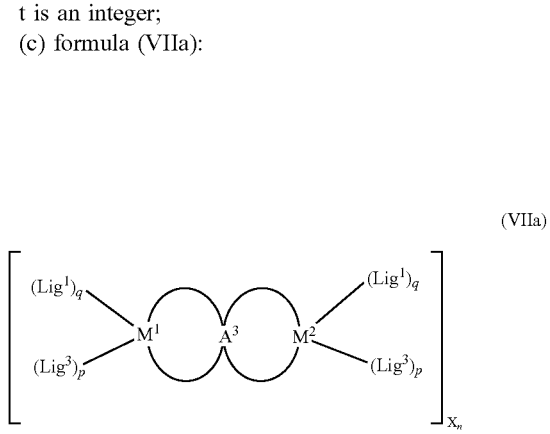

including hydrates, solvates, pharmaceutically acceptable salts, prodrugs and complexes thereof wherein:

$A^3$ is selected from the group consisting of

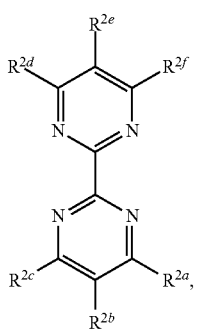

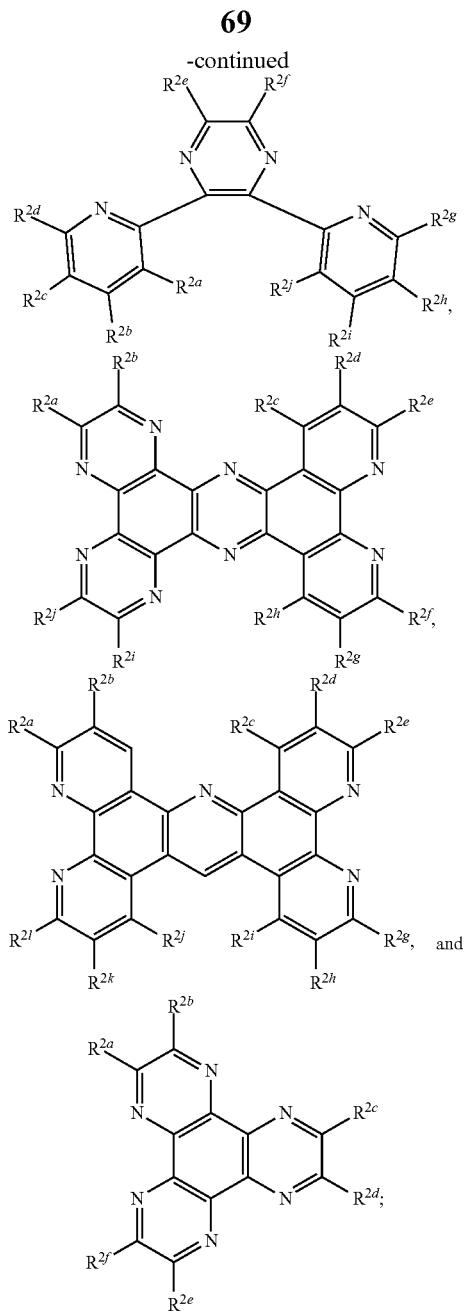
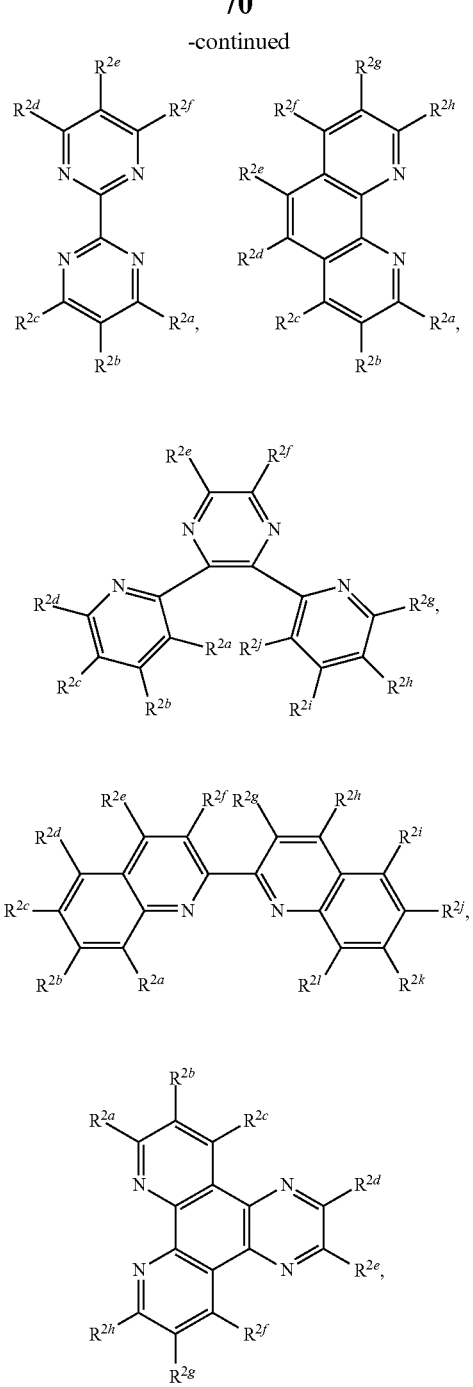
Lig¹ is a bidentate ligand that at each occurrence is each independently selected from the group consisting of
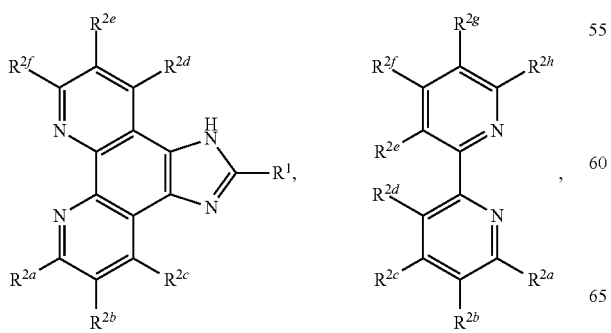

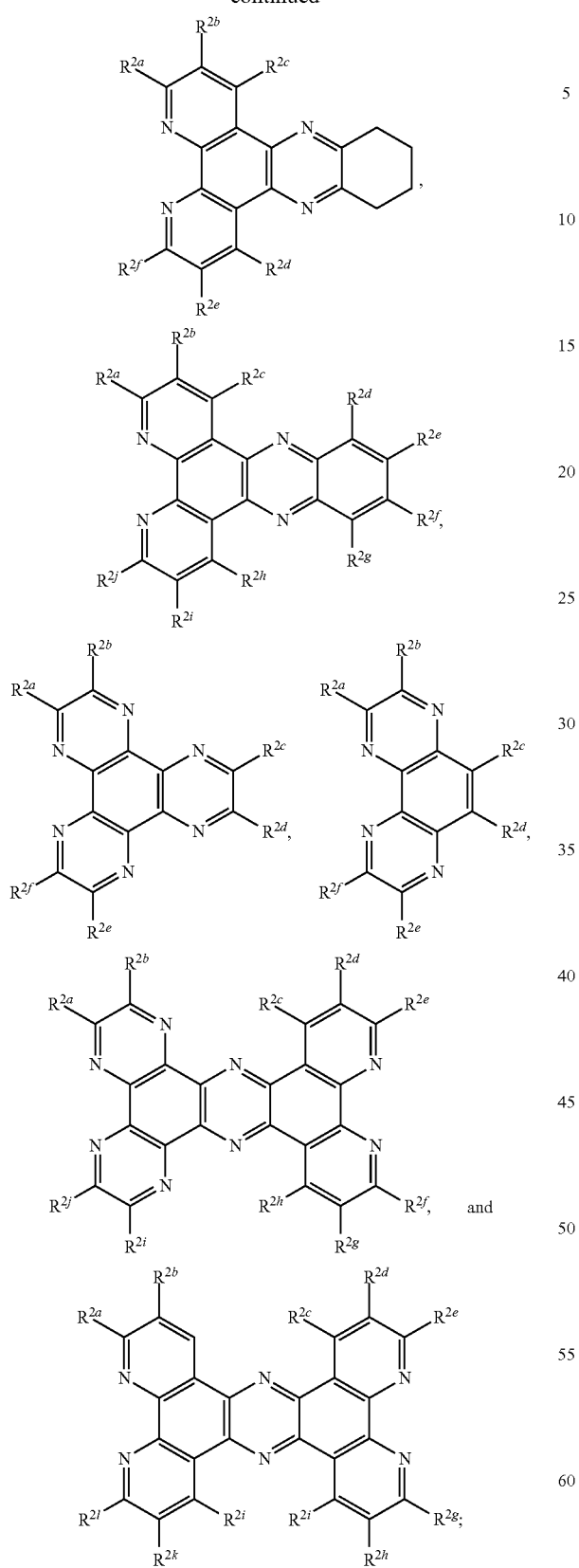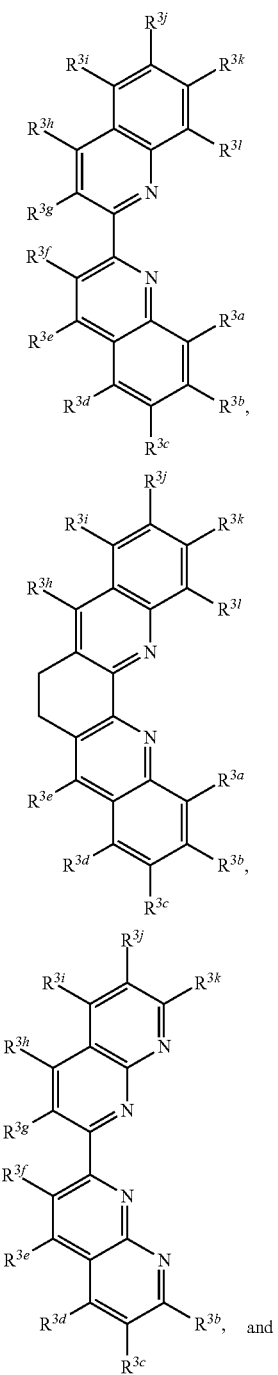
Lig³ is a bidentate ligand that at each occurrence is each independently selected from the group consisting of -continued
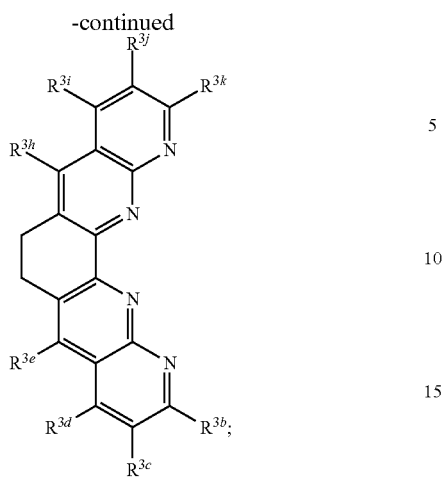
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
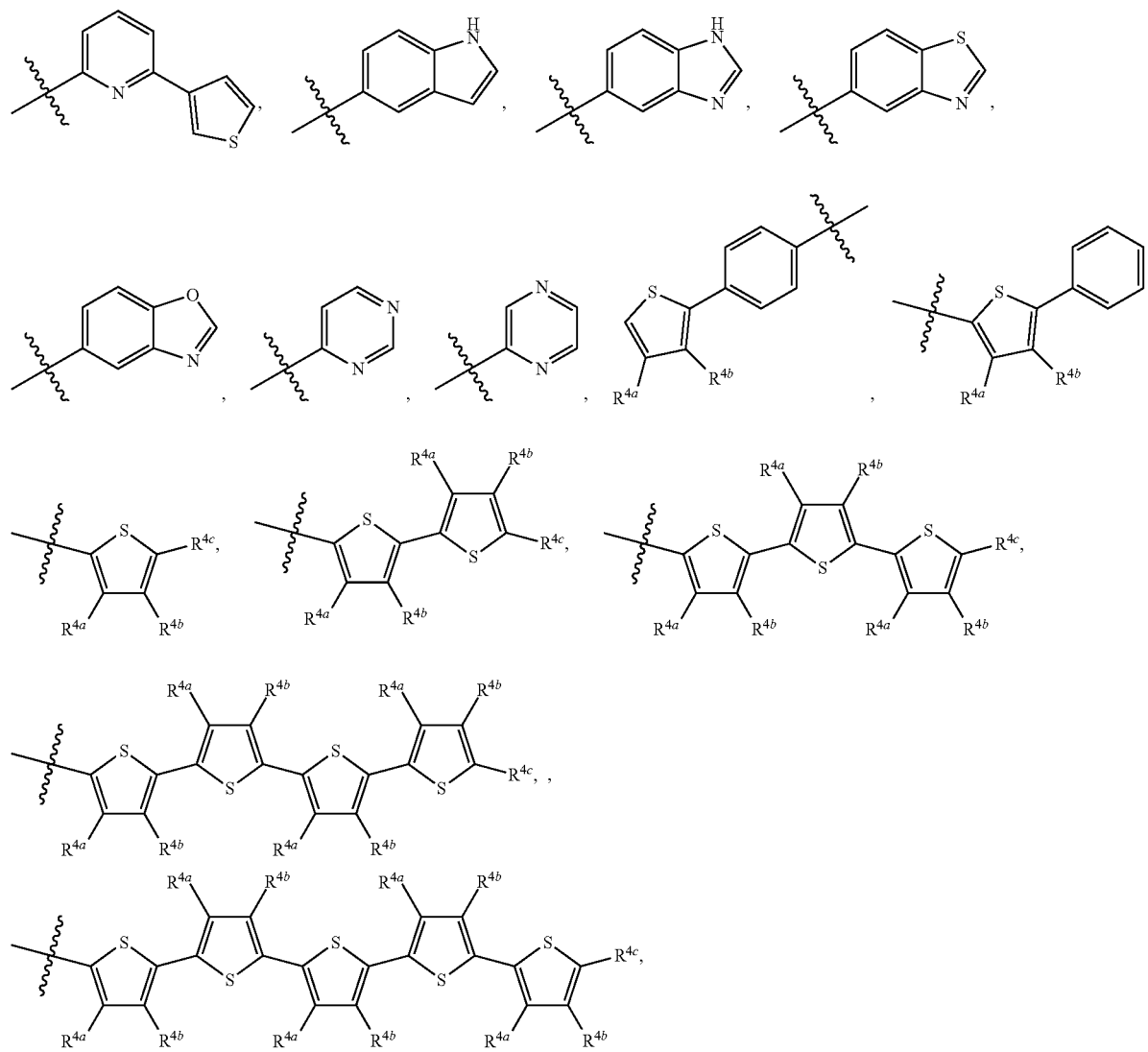

-continued

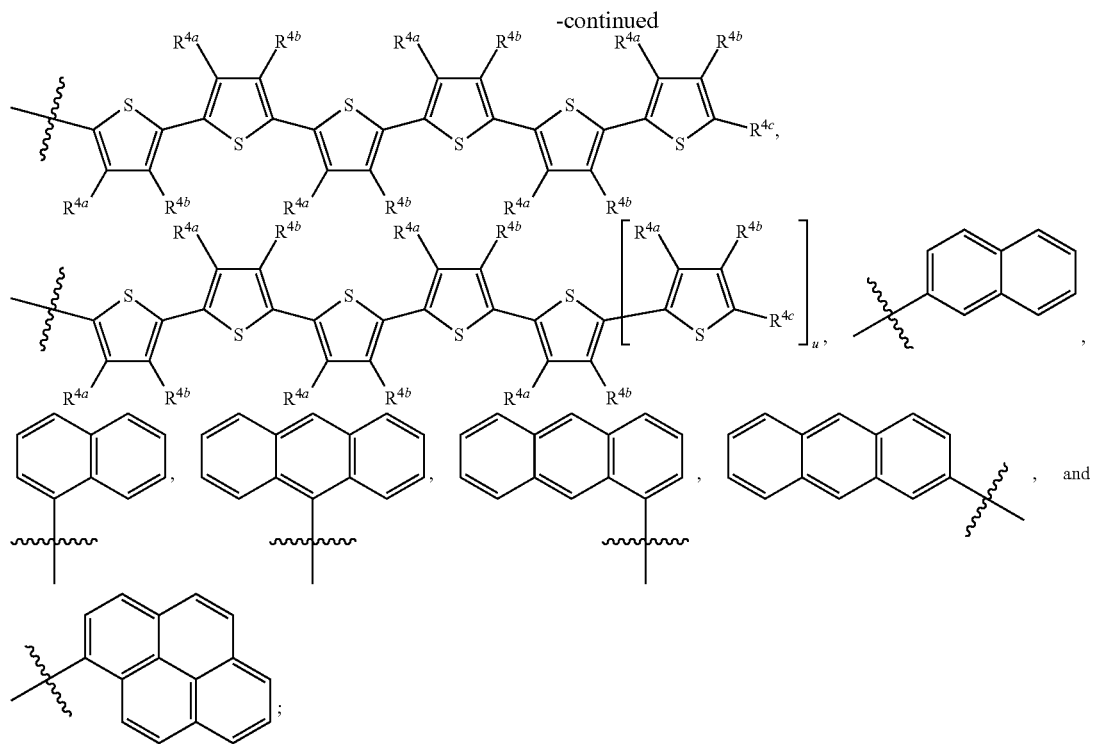

u is an integer;

$R^{2a}, R^{2b}, R^{2c}, R^{2d}, R^{2e}, R^{2f}, R^{2g}, R^{2h}, R^{2i}, R^{2j}, R^{2k},$ and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}, R^{3b}, R^{3c}, R^{3d}, R^{3e}, R^{3f}, R^{3g}, R^{3h}, R^{3i}, R^{3j}, R^{3k},$ and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl p is independently at each occurrence 0, 1, or 2;
q is independently at each occurrence 0, 1, or 2; and
n is 0, 1, 2, 3, 4, or 5;

(d) formula (II):

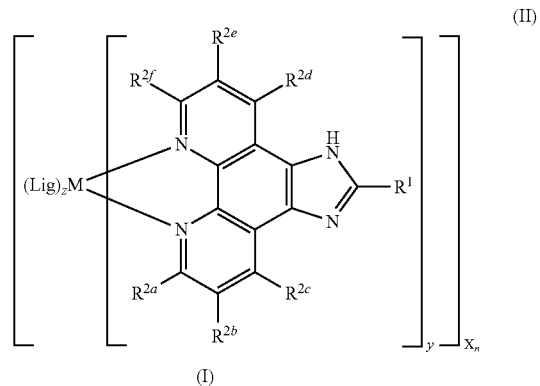

(II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;
y=1, 2, or 3;
z=0, 1, or 2;
Lig at each occurrence is independently selected from the group consisting of
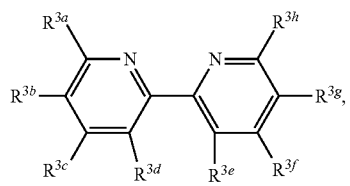
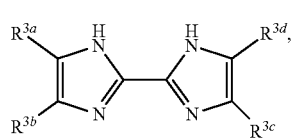
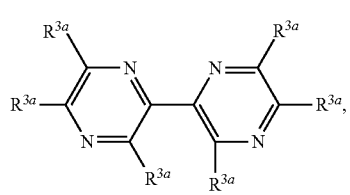
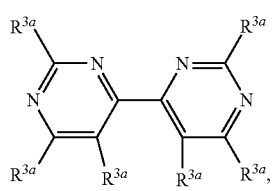
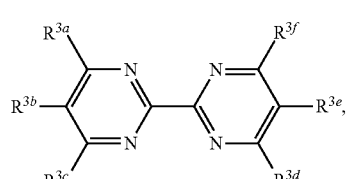
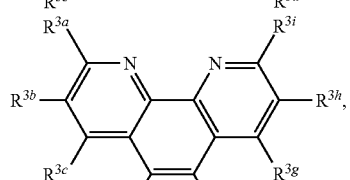
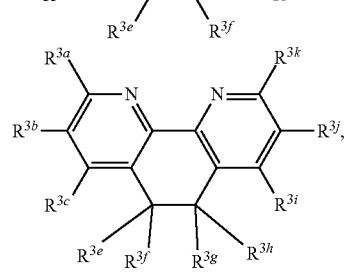
-continued
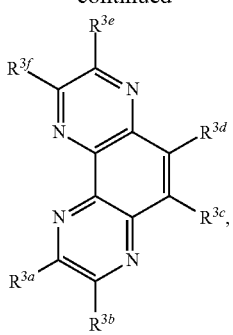
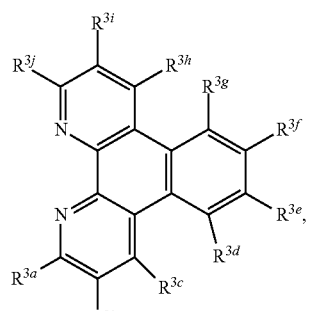
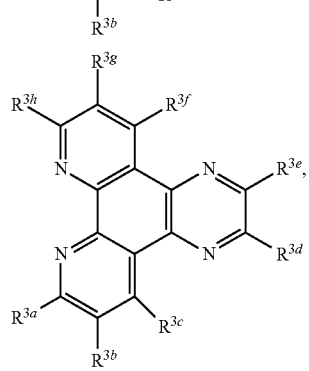
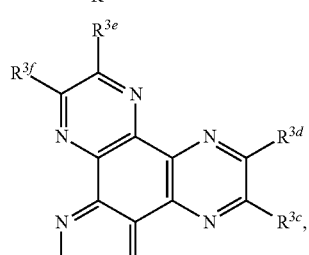
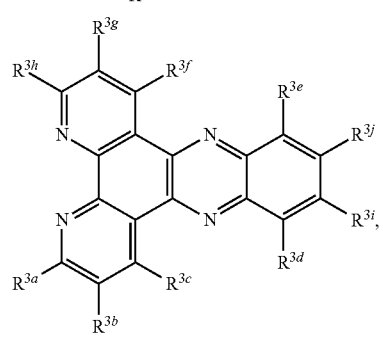

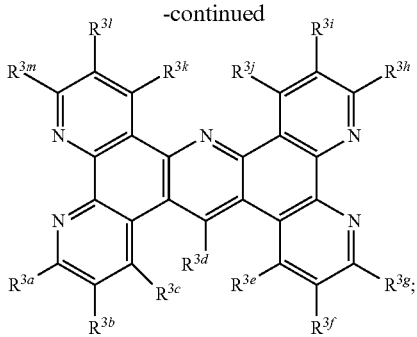
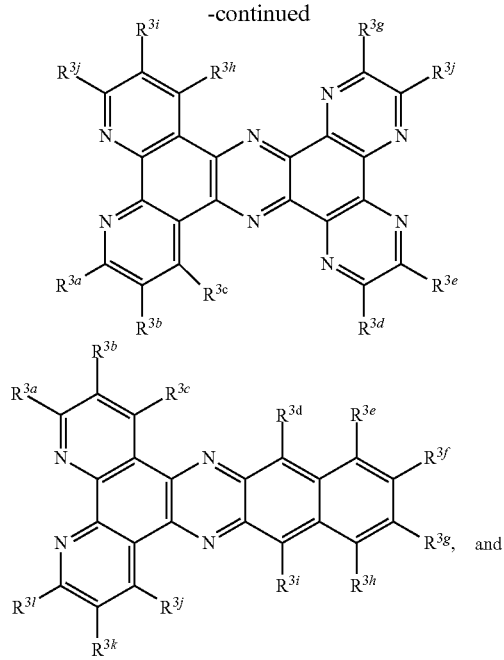
R[1] is selected from the group consisting of
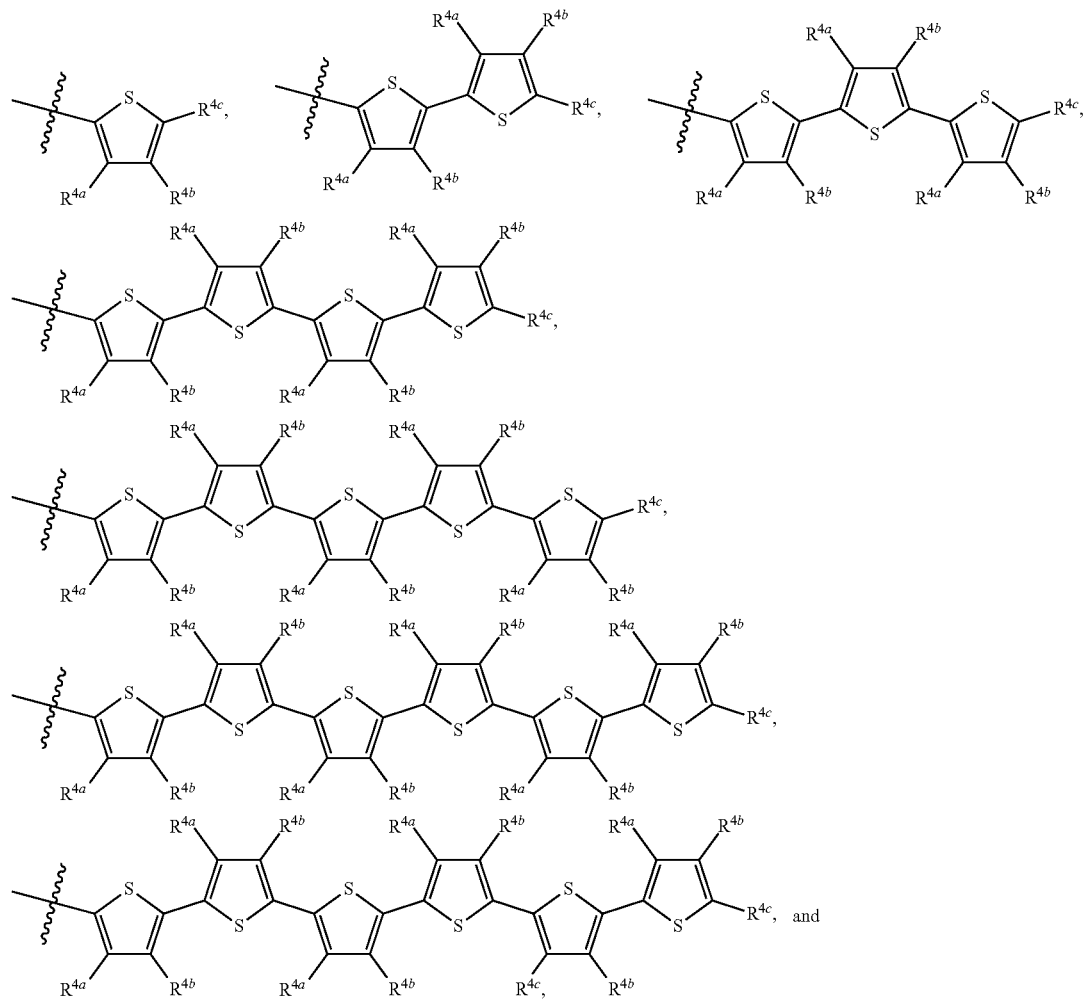

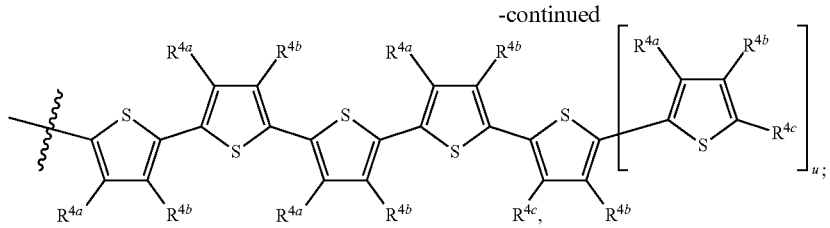

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

10. The method of claim 9, wherein the electromagnetic radiation is laser light having a wavelength from 500-950 nm.

11. The method of claim 9, wherein the electromagnetic radiation is X-rays or Gamma rays.

12. The method of claim 9, wherein the donor is a human and the tumor cells are cancer cells.

13. The method of claim 9, wherein the metal-based coordination complex further comprises transferrin.

14. The method of claim 9, wherein M is at least one of Ru, Rh, Os and Ir.

15. The method of claim 9, wherein the metal-based coordination complex has the following structure:

16. The method of claim 9, wherein the immunogenic composition is incubated with dendritic cells from the patient so as to prepare armed dendritic cells having tumor antigens, the armed dendritic cells are administered to the patient optionally in combination with transferrin, and/or the armed dendritic cells are co-cultured with CD4+ or CD8+ to provide expanded CD4+ or CD8+ cells which are administered to the patient optionally in combination with transferrin.

17. An immunogenic composition prepared by the method of claim 9.

18. The immunogenic composition of claim 17, wherein the metal-based coordination complex further comprises transferrin.

19. The immunogenic composition of claim 17, wherein M is at least one of Ru, Rh, Os and Ir.

20. The immunogenic composition of claim 17, wherein the metal-based coordination complex has the following structure:

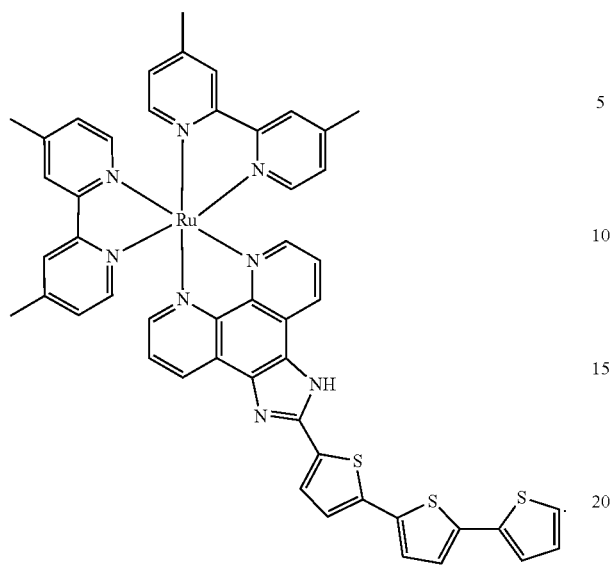
* * * * *